US008888674B2

(12) United States Patent
Shapiro et al.

(10) Patent No.: US 8,888,674 B2
(45) Date of Patent: Nov. 18, 2014

(54) METHODS AND SYSTEMS FOR MAGNETIC FOCUSING OF THERAPEUTIC, DIAGNOSTIC OR PROPHYLACTIC AGENTS TO DEEP TARGETS

(75) Inventors: Benjamin Shapiro, Washington, DC (US); Andreas Lüebbe, Paderborn (DE); Declan Diver, Glasgow (GB); Hugh Potts, Glasgow (GB); Roland Probst, Bobenheim-Roxheim (DE)

(73) Assignees: University of Maryland College Park, College Park, MD (US); University of Glasgow, Glasgow (GB)

( * ) Notice: Subject to any disclaimer, the term of this patent is extended or adjusted under 35 U.S.C. 154(b) by 973 days.

(21) Appl. No.: 12/747,070

(22) PCT Filed: Dec. 10, 2008

(86) PCT No.: PCT/US2008/086276
§ 371 (c)(1),
(2), (4) Date: Nov. 15, 2010

(87) PCT Pub. No.: WO2009/076465
PCT Pub. Date: Jun. 18, 2009

(65) Prior Publication Data
US 2011/0054237 A1   Mar. 3, 2011

Related U.S. Application Data

(60) Provisional application No. 60/996,931, filed on Dec. 11, 2007.

(51) Int. Cl.
*A61N 2/00* (2006.01)
*A61M 31/00* (2006.01)
*A61B 5/00* (2006.01)
*A61B 5/055* (2006.01)

(52) U.S. Cl.
CPC .............. *A61M 31/002* (2013.01); *A61N 2/002* (2013.01); *A61B 5/055* (2013.01); *A61B 5/411* (2013.01)
USPC .............. 600/12; 424/1.11; 424/9.1; 424/400

(58) Field of Classification Search
CPC ......... A61N 1/406; A61N 2/002; A61N 2/06; A61N 2/02; A61N 1/16; A61N 1/30; A61N 2/00; A61N 1/05; A61N 2005/063; A61N 2/004; A61N 2005/067; A61N 5/062
USPC ........... 600/9, 13, 15; 128/897–899; 424/422, 424/426
See application file for complete search history.

(56) References Cited

U.S. PATENT DOCUMENTS

| 4,662,359 A | 5/1987 | Gordon |
| 4,690,130 A | 9/1987 | Mirell |

(Continued)

FOREIGN PATENT DOCUMENTS

| WO | WO 03007996 | 1/2003 |
| WO | WO 03022360 | 3/2003 |

(Continued)

OTHER PUBLICATIONS

Earnshaw, S. (1842) "On the Nature of the Molecular Forces Which Regulate The Constitution of the Luminiferous Ether," Trans. Camb. Phil. Soc. 7:97-112.

(Continued)

*Primary Examiner* — Christine Matthews
*Assistant Examiner* — Joshua D Lannu
(74) *Attorney, Agent, or Firm* — William C. Schrot; Jeffrey I. Auerbach; AuerbachSchrot LLC

(57) ABSTRACT

Systems and methods are disclosed for trapping or focusing magnetizable particles comprising therapeutic agents at a distance using a dynamic magnetic field and feedback control, to enable the treatment of diseased areas deep inside a patient's body. The methods may be used to diagnose or treat diseased areas deep within a patient, for example tumors of the lungs, intestines, and liver, and is also useful in enhancing the permeability of solid tumors to chemotherapeutic agents.

28 Claims, 4 Drawing Sheets

(56) References Cited

U.S. PATENT DOCUMENTS

| | | | |
|---|---|---|---|
| 4,869,247 | A | 9/1989 | Howard, III et al. |
| 5,010,897 | A | 4/1991 | Leveen |
| 5,099,756 | A | 3/1992 | Franconi et al. |
| 5,203,782 | A | 4/1993 | Gudov et al. |
| 5,236,410 | A | 8/1993 | Granov et al. |
| 5,339,347 | A | 8/1994 | Slatkin et al. |
| 5,667,469 | A | 9/1997 | Zhang et al. |
| 5,835,995 | A | 11/1998 | Macovski et al. |
| 6,128,174 | A | 10/2000 | Ritter et al. |
| 6,241,671 | B1 | 6/2001 | Ritter et al. |
| 6,245,005 | B1 | 6/2001 | von Gutfeld et al. |
| 6,296,604 | B1* | 10/2001 | Garibaldi et al. .............. 600/12 |
| 6,298,259 | B1 | 10/2001 | Kucharczyk et al. |
| 6,315,709 | B1* | 11/2001 | Garibaldi et al. .............. 600/12 |
| 6,447,999 | B1 | 9/2002 | Giesen et al. |
| 6,470,220 | B1 | 10/2002 | Kraus, Jr. et al. |
| 6,475,223 | B1 | 11/2002 | Werp et al. |
| 6,546,279 | B1 | 4/2003 | Bova et al. |
| 6,776,165 | B2 | 8/2004 | Jin |
| 6,842,324 | B2 | 1/2005 | Eyssa |
| 7,074,175 | B2 | 7/2006 | Handy et al. |
| 2002/0147424 | A1 | 10/2002 | Ostrow et al. |
| 2003/0073879 | A1 | 4/2003 | Sandstrom |
| 2004/0030244 | A1* | 2/2004 | Garibaldi et al. ............ 600/424 |
| 2004/0156919 | A1 | 8/2004 | Lee |
| 2005/0019257 | A1 | 1/2005 | Kim et al. |
| 2005/0129727 | A1 | 6/2005 | Weber et al. |
| 2005/0267457 | A1 | 12/2005 | Hruschka |
| 2006/0041182 | A1* | 2/2006 | Forbes et al. ................... 600/12 |
| 2006/0176997 | A1 | 8/2006 | Dilmanian et al. |
| 2006/0188442 | A1 | 8/2006 | Hallihan et al. |
| 2007/0196281 | A1* | 8/2007 | Jin et al. ....................... 424/9.34 |

FOREIGN PATENT DOCUMENTS

| | | |
|---|---|---|
| WO | WO 2005065282 | 7/2005 |
| WO | WO 2007079276 | 7/2007 |
| WO | WO 2007113572 | 10/2007 |
| WO | WO 2007113572 A1 * | 10/2007 |
| WO | WO 2009076465 | 6/2009 |

OTHER PUBLICATIONS

Ritter, J.A. et al. (2004) "*Application of High Gradient Magnetic Separation Principles to Magnetic Drug Targeting,*" J. Magnetism and Magnetic Materials, 280:184-201 (2004).

Alexiou, C. et al. (2006) Targeting cancer cells: magnetic nanoparticles as drug carriers, Eur. Biophys. J. 35:446-450.

Avilés, M.O. et al. (2005) "*Theoretical Analysis of a Transdermal Ferromagnetic Implant for Retention of Magnetic Drug Carrier Particles,*" J. Magnetism and Magnetic Materials 293:605-615.

Denardo, S.J et al. (Oct. 1, 2005) Development of Tumor Targeting Bioprobes ($^{111}$In-Chimeric L6 Monoclonal Antibody Nanoparticles) for Alternating Magnetic Field Cancer Therapy, Clin Canc. Res. 11(19 Suppl.):7087S-7092S.

Furlani, E.P. et al. (Jun. 27, 2006) "Analytical model of magnetic nanoparticle transport and capture in the microvasculature", Phys. Rev. E 73:061919-1-061929-10.

Ganguly, R. et al. (2005) "*Analyzing Ferrofluid Transport for Magnetic Drug Targeting,*" J. of Magnetism and Magnetic Materials, 289:331-334.

Grief, A. D. et al. (2005) "*Mathematical Modelling of Magnetically Targeted Drug Delivery,*" J. of Magnetism and Magnetic Materials, 293:455-463.

Hafeli, U. O. et al. (2007) "*Modeling of Magnetic Bandages for Drug Targeting: Button vs. Halbach Arrays,*" J. of Magnetism and Magnetic Materials, 311:323-329.

Hafeli, U.O. (2004) "Magnetically modulated therapeutic systems", International Journal of Pharmaceutics 277: 19-24.

Iacob, G.H. et al. (2004) "*A Possibility for Local Targeting of Magnetic Carriers,*" J. Optoelectronics and Advanced Materials 6:713-717.

Iacob, G.H. et al. (2004) "*Magnetizable Needles and Wires—Modeling an Efficient Way to Target Magnetic Microspheres in vivo,*" Biorheology 41:599-612.

International Search Report and Written Opinion; PCT/US2008/086276 (WO 2009/076465) (2009)(12 pages).

Kenney, C. J. et al. (2006) "*Active-Edge Planar Radiation Sensors,*" Nuclear Instruments and Methods in Physics Research A, 565:272-277.

Lemke, M. I. et al., (2004) "*MRI After Magnetic Drug Targeting in Patients With Advanced Solid Malignant Tumors,*" Eur. Radiology, 14:1949-1955.

Lubbe, A. S. et al. (1996) "*Clinical Experiences With Magnetic Drag Targeting: A Phase I Study With 4'-Epidoxorubicin in 14 Patients With Advanced Solid Tumors,*" Cancer Res., 56:4686-4693.

Lubbe, A. S. et al. (1996) "*Preclinical Experiences With Magnetic Drug Targeting: Tolerance and Efficacy,*" Cancer Res., 56:4694-4701.

Martel, S. et al. (2007) "*Automatic Navigation of an Untethered Device in the Artery of a Living Animal Using a Conventional Clinical Magnetic Resonance Imaging System,*" Applied Physics Letters 90:114105.

Mathieu, J. B. et al. (2007) "*Magnetic Microparticle Steering Within the Constraints of an MRI System: Proof of Concept of a Novel Targeting Approach,*" Biomedical Microdevices, 9:801-808.

Parker, S. I. et al. (2006) "*3DX: An X-Ray Pixel Array Detector With Active Edges,*" IEEE Transactions on Nuclear Science, 53:1676-1688.

Potts, H. E. et al. (2001) "*Dynamics of Freely-Suspended Drops,*" J. of Physics D-Applied Physics, 34:2629-2636.

Potts, H.E. et al. (2001) "Ferrofluid Hydrodynamics: waves, Jets and Free Drops," Brazilian J. Phys. 31(3):433 -440.

Rosengart, A.J. et al. (2005) "*Magnetizable Implants and Functionalized Magnetic Carriers: A Novel Approach for Noninvasive Yet Targeted Drug Delivery,*" J. Magnetism and Magnetic Materials 293:633-638.

Rotariu, O. et al. (2005) "*Modelling Magnetic Carrier Particle Targeting in the Tumor Microvasculature for Cancer Treatment,*" J. Magnetism and Magnetic Materials, 293:639-647.

Shapiro, B. (2009) "Towards dynamic control of magnetic fields to focus magnetic carriers to targets deep inside the body," J. Magn. Magn. Mater. 321(10):1594; pp. 1-13.

University of Buffalo (UB) News Direct Online "Magnetic Field Acts as Remote Control to Delivery Nanomedicine", Jun. 6, 2006, pp. 1-3.

Urdea, L.E. et al. (2006) "An in vitro study of magnetic particle targeting in small blood vessels," Phys. Med. Biol. 51:4869-4881.

Voltairas, P. A. et al. (2002) "*Hydrodynamics of Magnetic Drug Targeting,*" Journal of Biomechanics, 35: 813-821.

Yellen, B.B. et al. (2005) "*Targeted Drug Delivery to Magnetic Implants for Therapeutic Applications,*" J. Magnetism and Magnetic Materials, 293:647-654.

Alexiou et al. (2000) "*Locoregional cancer treatment with magnetic drug targeting,*" Cancer Res. 60:6641-8.

* cited by examiner

METHODS AND SYSTEMS FOR MAGNETIC FOCUSING OF THERAPEUTIC, DIAGNOSTIC OR PROPHYLACTIC AGENTS TO DEEP TARGETS

CROSS-REFERENCE TO RELATED APPLICATIONS

This application is a 35 U.S.C. §371 Application of PCT/US2008/086276 (filed on Dec. 10, 2008, pending) and claims priority to U.S. Patent Application Ser. No. 60/996,931 (filed on Dec. 11, 2007; lapsed), which applications are herein incorporated by reference in their entireties.

BACKGROUND OF THE INVENTION

1. Field of the Invention

This invention relates generally to targeted magnetic therapeutic systems and methods, and specifically, to systems and methods for using a dynamic magnetic field to focus magnetizable therapeutic, diagnostic or prophylactic agents to deep tumors within a patient's body.

2. Description of Related Art

Cancer is a major cause of death in the United States, claiming more than 500,000 lives each year according to American Cancer Society estimates. The primary treatment options for cancer are surgery, radiation therapy, chemotherapy, and immunotherapy. Although surgical removal of a tumor is usually the favored option, some tumors are inoperable, for example because they are inaccessible or have ill-defined borders. Thus, radiation therapy, chemotherapy, and immunotherapy are often used to treat cancer in conjunction with, or instead of, surgery.

Radiation therapy, chemotherapy, and immunotherapy can achieve some success in treating many cancers, but these treatments have disadvantages as well. For example, radiation therapy has limited success because hypoxic cancer cells in solid tumors are able to fix the DNA damage caused by radiation, and therefore are resistant to radiation therapy. Immunotherapy also has disadvantages, in that non-tumor cells can be damaged, delivery to tumor cells may be inefficient, and toxicity may be unacceptably high. Chemotherapy remains a primary treatment for cancer, but also has disadvantages, including poor delivery and cellular uptake of chemotherapeutic agents into malignant tissue, drug resistance and non-specific toxicity. Further, the dosage of chemotherapeutic agents is usually limited to a dosage that is low enough not to kill the patient, however such a dosage may not be high enough to kill all malignant cells.

Poor delivery of therapeutic agents to diseased cells is a difficult problem in cancer treatment, especially treatment of cancers deep within the body. Even when the agents are delivered to the locale of the tumor mass, poor penetrability into the tumor mass may require prolonged high dose treatment, and subsequent severe systemic adverse effects. For these reasons, it is desirable to provide improved and alternative techniques for treating disease, particularly techniques that are less invasive and traumatic to the patient than the existing techniques, and are able to be targeted to diseased tissue in the body. The promise of targeted drug delivery is that therapeutic agents can be targeted to diseased tissue, thereby enabling high concentrations at the tumor, with lower concentrations elsewhere in the body. The ability to focus therapeutic agents to specific locations is useful not only for cancer treatment, but also for the treatment of diseases or disorders that are localized in the body, for example a localized infection such as a spinal abscess or restenosis in a coronary artery.

Targeted delivery techniques are being explored for the treatment of cancers and other diseases, and include three primary approaches: passive targeting, active targeting, and physical targeting. Passive targeting techniques rely on selective accumulation of drugs at the tumor site due to differences between healthy and tumor cells, for example the Enhanced Permeability and Retention (EPR) effect, or on localized delivery, for example direct intratumoral delivery in prostate cancer treatment. Active targeting techniques include conjugating the therapeutic agent to a targeting ligand, such as RGD peptides, and tumor-specific antibodies. Physical targeting techniques include stimulating tumor tissue with ultrasonic waves, which promotes intracellular drug uptake.

Magnetic drug delivery has also been attempted, in which drugs are attached to magnetic particles, and then externally applied magnetic fields from stationary magnets outside the body are used to focus the drugs to specific locations near the surface of the body. Magnetic drug particles for treatment of shallow tumors have been tested for safety and efficacy in animal and human clinical trials, where particles are injected into a vein, distributed throughout the body by the circulatory system, and then captured and concentrated at the desired shallow tumor location by a strong stationary magnet held near the tumor. Direct injection of magnetic particles into a tumor, followed by thermal excitation of the magnetic particles, has also been attempted with some success in the treatment of prostate cancers. However, non-invasive magnetic drug delivery to deep tissue such as the lungs, intestines, and liver, has not been successful because the magnetic fields necessary to overcome blood flow rates in the arteries, and to target the nanoparticles more than about 5 centimeters inside the body, generally exceed the threshold (~1-2 Tesla) of what is considered safe for human application. Thus, conventional means of magnetic drug targeting has not proven successful with deep tissue tumors.

What is needed are improved magnetic drug delivery methods and systems that overcome these difficulties and results in improved focusing of magnetic therapeutic agents, particularly for the treatment of deep tissue tumors.

SUMMARY OF THE INVENTION

The present invention relates to methods and systems for focusing of therapeutic, diagnostic or prophylactic agents to deep tumors using a dynamic magnetic field that varies in both space and time. The present invention also relates to methods and systems for treating a patient comprising administering a plurality of magnetizable nano-objects to a patient and applying a dynamic magnetic field to the patient in order to focus the plurality of magnetizable nano-objects to a deep target area within the patient. Further provided are methods and systems for treating a patient comprising administering a ferrofluid comprising a plurality of magnetizable nano-objects to a patient and applying a dynamic magnetic field to the patient in order to focus the ferrofluid to a deep target area within the patient, and determining the effectiveness of said focusing over a period of time by detecting at least one concentration or location of the ferrofluid within the patient at different times.

Also provided by the present invention are methods and systems for treating a patient comprising administering a plurality of magnetizable nano-objects comprising a therapeutic agent to a patient, applying a dynamic magnetic field to the patient, detecting at least one location of accumulation of the plurality of magnetizable nano-objects within the patient, and adjusting the dynamic magnetic field in order to focus the plurality of magnetizable nano-objects on a target area that is at least 5 centimeters inside the patient.

In detail, the invention provides a method for treating a patient comprising, the steps:
(A) administering a plurality of magnetizable objects to a patient;
(B) externally applying a dynamic magnetic field to the patient in order to focus the plurality of magnetizable objects to a deep target area within the patient.

The invention additionally concerns the embodiment of such method wherein the plurality of magnetizable objects comprises magnetizable component of a ferrofluid, and wherein, in the step (B) the external application of the dynamic magnetic field focuses the ferrofluid to a deep target area within the patient; and wherein the method additionally comprises the step:
(C) determining the effectiveness of the focusing over a period of time by detecting at least one location of the ferrofluid within the patient at different times.

The invention additionally concerns the embodiments of such methods wherein the plurality of magnetizable objects comprises a therapeutic agent; and wherein the method comprises the steps:
(A) administering a plurality of magnetizable objects to a patient;
(B) externally applying a dynamic magnetic field to the patient in order to focus the plurality of magnetizable objects to a deep target area within the patient.
(C) detecting at least one location of the plurality of magnetizable objects within the patient; and
(D) adjusting the dynamic magnetic field based on the detection.

The invention additionally concerns the embodiment of such method wherein the method additionally comprises the step:
(E) focusing the magnetizable objects to a target area of the patient that is at least 5 centimeters inside the patient by external application of the magnetic field.

The invention additionally concerns the embodiments of such methods wherein in the step (D), the deep target area is at least 5 centimeters inside the patient.

The invention additionally concerns the use of a plurality of magnetizable objects comprising a therapeutic agent for the manufacture of a medicament for the therapeutic, diagnostic or prophylactic treatment of a medical condition, wherein the medicament can be focused to a deep target area within a patient by external application of a magnetic field.

The invention additionally concerns the embodiment of such use wherein the plurality of magnetizable objects comprises a ferrofluid.

The invention additionally concerns the embodiment of such method wherein the medicament permits the deep target area to be at least 5 centimeters inside the patient.

The invention additionally concerns the embodiments of such uses wherein the magnetizable objects are between about 1 µm and 1 mm in diameter, and more preferably, wherein the magnetizable objects are between about 1 µm and 1 nm in diameter.

The invention additionally concerns the embodiments of such methods or said uses wherein the plurality of magnetizable objects is a magnetizable component of a ferrofluid.

The invention additionally concerns the embodiments of such methods wherein the administering step comprises injecting the plurality of magnetizable objects into the patient.

The invention additionally concerns the embodiments of such methods or said uses wherein the magnetizable objects comprise a therapeutic, diagnostic or prophylactic agent.

The invention additionally concerns the embodiments of such methods or said uses wherein the magnetizable objects comprise a detectable label.

The invention additionally concerns the embodiments of such methods or said uses wherein the detectable label is a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label.

The invention additionally concerns the embodiments of such methods wherein the dynamic magnetic field has a rate of change of up to about 20 Tesla/second.

The invention additionally concerns the embodiments of such methods or said uses wherein the deep target area is associated with a cancer, a disease of the vascular system, an infection, or non-cancerous disease material.

The invention additionally concerns the embodiments of such methods or said uses wherein the deep target area is located at least 5 centimeters inside the patient.

The invention additionally concerns the embodiments of such methods further comprising detecting at least one location of the plurality of magnetizable objects within the patient.

The invention additionally concerns the embodiments of such methods wherein the detecting comprises using magnetic resonance imaging.

The invention additionally concerns the embodiments of such methods or said uses wherein the magnetizable objects comprise a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label, and wherein the detecting detects the label.

The invention additionally concerns the embodiments of such methods further comprising a feedback controller to control the dynamic magnetic field in response to the detection.

The invention additionally concerns the embodiments of such methods wherein the effectiveness of the focusing is measured over a period of time.

The invention additionally provides a device for externally applying a dynamic magnetic field to a patient sufficient to focus a plurality of magnetizable objects, or a ferrofluid composed thereof, to a deep target area within the patient, wherein the device comprises:
(A) an array of independently operable magnets, where the magnets may be permanent magnets, electromagnets, or a combination thereof;
(B) a sensor system capable of detecting at least one location of a plurality of magnetizable objects within the patient; and
(C) a Dynamic Magnetic Field generator capable of dynamically and individually controlling the direction and strength of the magnetic fields of the magnets to thereby focus the plurality of magnetizable objects to the deep target area within the patient.

The invention additionally concerns the embodiments of such device wherein the deep target area is at least 5 centimeters inside the patient.

The invention additionally concerns the embodiments of such devices wherein the magnetizable objects are between about 1 μm and 1 mm in diameter and more preferably wherein the magnetizable objects are between about 1 μm and 1 nm in diameter.

The invention additionally concerns the embodiments of such devices wherein the magnetizable objects comprise a therapeutic, diagnostic or prophylactic agent.

The invention additionally concerns the embodiments of such devices wherein the magnetizable objects comprise a detectable label and the device additionally comprises:

(D) a detector capable of detecting the detectable label.

The invention additionally concerns the embodiments of such devices wherein the detector (D) is capable of detecting a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label.

The invention additionally concerns the embodiments of such devices wherein the Dynamic Magnetic Field generator (C) is capable of causing a dynamic magnetic field rate of up to about 20 Tesla/second.

The invention additionally concerns the embodiments of such devices wherein the device additionally comprises:

(E) a feedback controller to control the dynamic magnetic field in response to the detection of the detectable label.

The invention additionally concerns the embodiments of such devices wherein the device additionally measures effectiveness of the focusing over a period of time.

Additional advantages and features of the present invention will be apparent from the following detailed description, drawings and examples, which illustrate preferred embodiments of the invention.

DETAILED DESCRIPTION OF THE INVENTION

Figure 1:
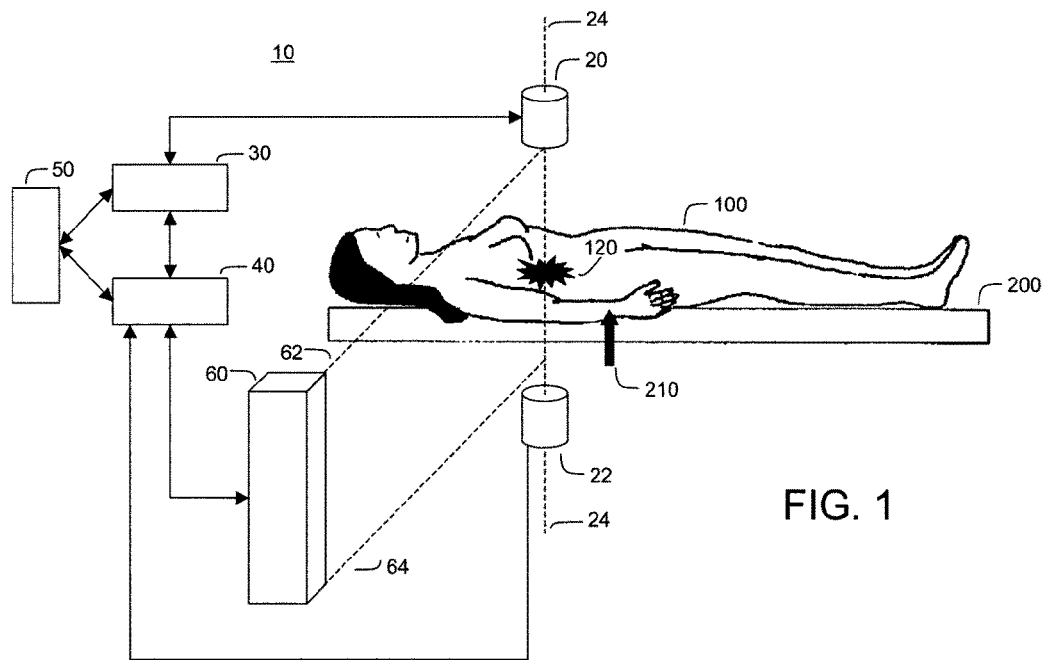
FIG. 1 is a schematic view of a dynamic magnetic focusing treatment system according to an embodiment of the present invention.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, electrical, biological, chemical, and control algorithm changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

In conventional magnetic drug therapy, an external magnet is held outside the body to focus magnetic or magnetizable particles. Conventional magnetic drug delivery relies on static magnetic fields, in which particles are attracted solely to regions of highest magnetic field gradients. This can be illustrated by the following equations. The force density (units $N/m^3$) on a fluid element of a ferrofluid is determined by Equation (1):

$$\vec{f}_{mag} = \frac{2\pi a^3}{3}\mu_0 C \frac{x}{1+\chi/3}\nabla(\vec{H}^2) \quad [\text{unsaturated}, \mu_0|\vec{H}|<0.1T] \quad (1)$$

$$= C\frac{4\pi a^3}{3}\mu_0 \vec{M}_{sat}\cdot\nabla\vec{H} \quad [\text{saturated}, \mu_0|\vec{H}|\geq 0.1T]$$

where a is the radius of the particles, $\mu_0=4\pi\times10^{-7}$ V s/A, m is the permittivity of vacuum, C is the local concentration of particles (number per $m^3$), $\chi$ is the magnetic susceptibility (a material property, nondimensional), and H in SI units A/m is the externally applied magnetic field strength. The first equation holds when the applied field is low (<0.1 Tesla). For higher fields, the magnetization saturates to $M_{sat}$~90 A $m^2$/kg at body temperature (because M lines up with H, by the chain rule $\nabla H^2$ and $M_{sat}\nabla H$ will point in the same directions). The magnetic forces go as the gradient of the applied magnetic field squared. The force-per-particle is very small: a single 250 nm diameter magnetite core particle under a 0.5 Tesla magnetic field varying over a length-scale of ~1 cm will experience a force of just ~$10^{-13}$ Newtons.

Because the highest magnetic gradients occur at the corners of such a magnet, the particles will get as close to the magnet as they can without leaving the body and thus concentrate at the skin surface. As a result, even with the highest 1-2 Tesla magnetic fields considered safe for human application, the particles cannot be focused to tumor targets deeper than about 5 centimeters into the body by conventional means. Thus, deep tissue targets such as tumors in the lungs, intestines, or liver cannot be treated using conventional magnetic therapy. This problem is a direct consequence of Earnshaw's Theorem, which states that static magnetic forces cannot produce a stable equilibrium of magnetizable objects at a distance.

A. Systems and Methods for Dynamic Magnetic Focusing

The present inventors have solved the problems in conventional magnetic therapy by developing methods and systems for trapping or focusing magnetizable objects at a distance using a dynamic magnetic field and feedback control. Embodiments of the present invention rely on creating a feedback control trap at tumor locations within a patient's body, and using a dynamic magnetic field created by sets of opposing magnets to bypass Earnshaw's Theorem. Thus, when magnetizable objects are injected into a patient's blood, they circulate throughout the body via the circulatory system and are caught by the dynamic magnetic trap and concentrated at the tumor site. The sensing required for feedback control is provided, for example, by magnetic resonance (MR) sensing, radioactive sensing, sensing of gamma rays emitted by the objects, etc.

Therefore, using the embodiments of the present invention, magnetizable compositions (e.g., chemotherapeutic agents attached to magnetizable particles) can be focused to tumors or other diseased tissue deep in a patient's body by an externally applied dynamic magnetic field, ensuring high concentrations at tumor locations, and lower concentrations elsewhere in the patient's body. The advantages of the magnetic focusing system and methods of the present invention include: reduced expense, because smaller amounts of therapeutic agents are required; enhanced efficacy of therapeutic agents with short half lives, because the agents can be concentrated to their targets quickly; and the ability to use more highly-toxic therapeutic agents than could be used with conventional chemotherapy delivery methods.

Referring now to FIG. 1, an exemplary embodiment of the dynamic magnetic focusing treatment system of the present invention is shown. The therapeutic methods may be performed on a patient 100 following a determination of the presence of diseased material 120 (e.g., a tumor, infection, abcess, stenotic lesion, etc.) in the patient. The system 10 is designed with opposing magnets 20, 22 arranged around a patient 100 such that the magnetic axis 24 of the magnets passes through the diseased material 120. The gap between magnets 20, 22 therefore must be large enough to permit a patient's body or body part to be inserted between the magnets. The patient may be arranged on bed 200 as necessary to achieve effective positioning of the system 10 relative to the area to be treated.

Magnetizable objects may be administered to the patient by any suitable means, exemplified here by intravenous injection 210 into the blood vessels of the arm. Depending on the type and location of the diseased tissue, suitable administration methods may include, but are not limited to, ocular, intranasal, inhalation, oral, buccal, sublingual, mucosal, rectal, topical, transdermal, subcutaneous, intra-arterial, intravenous, intramuscular, intraperitoneal, parenteral, or infusion methodologies. Administration can be localized, for example by injecting the magnetizable objects into, or near, the tumor location, or systemic, for example intravenous injection.

In FIG. 1, magnets 20, 22 are connected to a Dynamic Magnetic Field (DMF) generator 30, and also to a feedback controller 40, both of which are connected to a control computer 60. The DMF generator 30 produces current to magnets 20, 22, and varies the current as directed by feedback controller 40 and/or control computer 50 such that the strength of magnets 20, 22 is varied, thereby creating a dynamic magnetic field around the area to be treated in the patient. The magnetic field is varied in both space and time in order to focus the magnetizable objects to the diseased material 120 in the patient's body.

The location and concentration of the magnetizable objects within the patient's body 100 are monitored by a sensor system 60, which may operate by any suitable means, such as magnetic resonance, radiation sensing (e.g., sensing of x-rays, gamma rays, etc.), ultrasound, or the like. A non-limiting example of a magnetic resonance sensor system is shown here, which creates an image plane shown here bounded by lines 62, 64, and magnetic axis 24, thereby collecting data regarding the position of the magnetizable objects in the patient's body. Feedback controller 40 uses the data collected by the sensor system 60 to direct the DMF generator 30 to vary the magnetic field in order to guide the movement of the magnetizable objects as desired, for example toward the diseased material 120. An operator or technician may control or monitor the object position and concentration via control computer 50. As noted above, the task of controlling many magnetizable objects, or a magnetizable fluid, to a target is more difficult that controlling a single object to a target. It is understood to a person skilled in the art that while attempting to control one object, all other objects may be driven away from the target. A control method is needed that control all, or a majority of the, magnetizable objects at once. Currently, there is no prior-art that enables such simultaneous control of many magnetizable objects to a deep target enabled by the below preferred embodiment.

The sensor system may additionally or alternatively be capable of detecting a detectable label that may be a component of, or associated with, the magnetizable objects or the ferrofluid containing such objects. The detectable label may be, for example, a radioisotopic label (e.g., $^{213}$Bi, $^{11}$C, $^{14}$C, $^{51}$Cr, $^{55}$Co, $^{57}$Co, $^{60}$Co, $^{64}$Cu, $^{165}$Dy, $^{169}$Er, $^{18}$F, $^{66}$Ga, $^{67}$Ga, $^{166}$Ho, $^{1}$H, $^{111}$In, $^{123}$I, $^{125}$I, $^{131}$I, $^{192}$Ir, $^{59}$Fe, $^{81}$Kr, $^{177}$Lu, $^{99}$Mo, $^{13}$N, $^{15}$O, $^{103}$Pd, $^{32}$P, $^{42}$K, $^{186}$Re, $^{188}$Re, $^{81}$Rb, $^{82}$Rb, $^{153}$Sm, $^{75}$Se, $^{24}$Na, $^{89}$Sr, $^{92}$Sr, $^{99m}$Tc, $^{201}$Tl, $^{133}$Xe, $^{169}$Yb, $^{177}$Yb, $^{90}$Y), a paramagnetic label (e.g., $^{1}$H, $^{13}$C, Cr (III), Co (II), Cu (II), Dy (III), Er (III), Gd (III), Ho (III), Fe (II), Fe (III), Mn (II), Nd (III), Ni (II), Pr (III), Sm (III), Tb (III), Yb (III), etc.) (such labels are preferably chelated to chemical ligands diethylene triamine pentaacetic acid (DTPA), 1,4,7, 10-tetraacetic acid (DOTA), 10-(2-hydroxypropyl) 1,4,7-triacetic acid (HPDO3A), 4,7-triacetic acid (DO3A)), a CARS (coherent anti-Stokes Raman Spectroscopy)-detectable label (see, e.g., Cheng, J. X. (2007) "*Coherent Anti-Stokes Raman Scattering Microscopy*," Appl. Spectrosc. 61(9):197-208; Müller, M. et al. (2007) "*Coherent Anti-Stokes Raman Scattering Microscopy*," Chemphyschem. 8(15):2156-2170; Holtom, G. R. et al. (2001) "*Achieving Molecular Selectivity In Imaging Using Multiphoton Raman Spectroscopy Techniques*," Traffic 2(11):781-788), a multiphoton fluorescence microscopy-detectable label (Pierce, M. C. et al. (2008) "*Optical Contrast Agents And Imaging Systems For Detection And Diagnosis Of Cancer*," Int. J. Cancer 123(9):1979-1990; Nemoto, T. (Epub 2008 Jun. 26) "*Living Cell Functions And Morphology Revealed By Two-Photon Microscopy In*

*Intact Neural And Secretory Organs*," Mol. Cells 26(2):113-120; Benninger, R. K. et al. (2008) "*Multi-Photon Excitation Imaging Of Dynamic Processes In Living Cells And Tissues*," Rev. Physiol. Biochem. Pharmacol. 160:71-92; Eichhoff, G. et al. "*In Vivo Calcium Imaging Of The Aging And Diseased Brain*," Eur. J. Nucl. Med. Mol. Imaging 35 Suppl 1:S99-106), a harmonic microscopy-detectable label (especially a second and third harmonic microscopy detectable label) (see, e.g., Lin, S. J. et al. (Epub 2007 Aug. 2) "*Multiphoton Microscopy: A New Paradigm In Dermatological Imaging*," Eur. J. Dermatol. 17(5):361-366; Botvinick, E. L. et al. (2007) "*Laser-Based Measurements In Cell Biology*," Methods Cell. Biol. 82:81-109; Werkmeister, E. et al. (2007) "*Multiphoton Microscopy For Blood Vessel Imaging: New Non-Invasive Tools (Spectral, SHG, FLIM)*," Clin. Hemorheol. Microcirc. 37(1-2):77-88; Débarre, D. et al. (2006) "Second- and third-harmonic generation microscopies for the structural imaging of intact tissues," Med. Sci. (Paris) 22(10):845-850; Sacconi, L. et al. (2006) "Cell imaging and manipulation by nonlinear optical microscopy," Cell. Biochem. Biophys. 45(3):289-302), an acoustic imaging-detectable label (see, e.g., Villanueva, F. S. (2008) "*Molecular Imaging Of Cardiovascular Disease Using Ultrasound*," J. Nucl. Cardiol. 15(4):576-586; Kaufmann, B. A. et al. (Epub 2007 Jan. 22) "*Molecular Imaging With Targeted Contrast Ultrasound*," Curr. Opin. Biotechnol. 18(1):11-16; Cosgrove, D. et al. (2004) "*Liver Tumors: Evaluation With Contrast-Enhanced Ultrasound*," Abdom. Imaging 29(4):446-454; Lindner, J. R. (2002) "*Evolving Applications For Contrast Ultrasound*," Amer. J. Cardiol. 90(10A):72J-80J; Lencioni, R. et al. (2002) "*Tissue Harmonic And Contrast-Specific Imaging: Back To Gray Scale In Ultrasound*," Eur. Radiol. 12(1):151-165), an impedance spectroscopy-detectable label (see, e.g., Lisdat, F. et al. (Epub 2008 Apr. 16) "*The Use Of Electrochemical Impedance Spectroscopy For Biosensing*," Anal. Bioanal. Chem. 391(5):1555-1567; Pänke, O. et al. (2008) "*Impedance Spectroscopy And Biosensing*," Adv. Biochem. Eng. Biotechnol. 109:195-237; Halter, R. J. et al. (Epub 2008 Mar. 4) "*Electrical Impedance Spectroscopy Of Benign And Malignant Prostatic Tissues*," J. Urol. 179(4):1580-1586), or a reflectance spectroscopy-detectable label (see, e.g., Sokolov, K. et al. (2002) "*Optical Spectroscopy For Detection Of Neoplasia*," Curr. Opin. Chem. Biol. 6(5):651-658; Franck, P. et al. (1998) "*Applications Of Infrared Spectroscopy To Medical Biology*," Cell. Mol. Biol. (Noisy-le-grand) 44(2):273-275; Gebhart, S. C. et al. (2007) "*Liquid-Crystal Tunable Filter Spectral Imaging For Brain Tumor Demarcation*," Appl. Opt. 46(10):1896-1910; Parekh, D. J. et al. (2006) "*In Vivo Assessment Of Radio Frequency Induced Thermal Damage Of Kidney Using Optical Spectroscopy*," J. Urol. 176(4 Pt 1):1626-1630; Lin, W. C. et al. (2005) "*In Vivo Optical Spectroscopy Detects Radiation Damage In Brain Tissue*," Neurosurgery 57(3):518-525).

In a preferred embodiment, sensor system 60 is a gamma camera able to detect the in vivo position of the magnetizable objects via their emission of gamma rays. Suitable gamma cameras are commercially available, for example from Nuclear Imaging Services and Nuclear Cardiology Systems. As of 2005, CCD gamma cameras were capable of achieving 0.1 mm resolution at 10 frames per second, and are expected to improve resolution and speed in the future. Currently, gamma cameras are better able to approach real-time feedback than magnetic resonance imaging, which is comparatively slow. However, the type of sensor system chosen may depend not only on the speed of feedback desired, but the magnetizable object composition as well. Objects for use with a gamma camera must be radioactive and emit gamma rays, which could be disadvantageous for certain patients. Likewise, x-rays, ultrasound, or other sensing means may be used to provide positional feedback.

Figure 2:
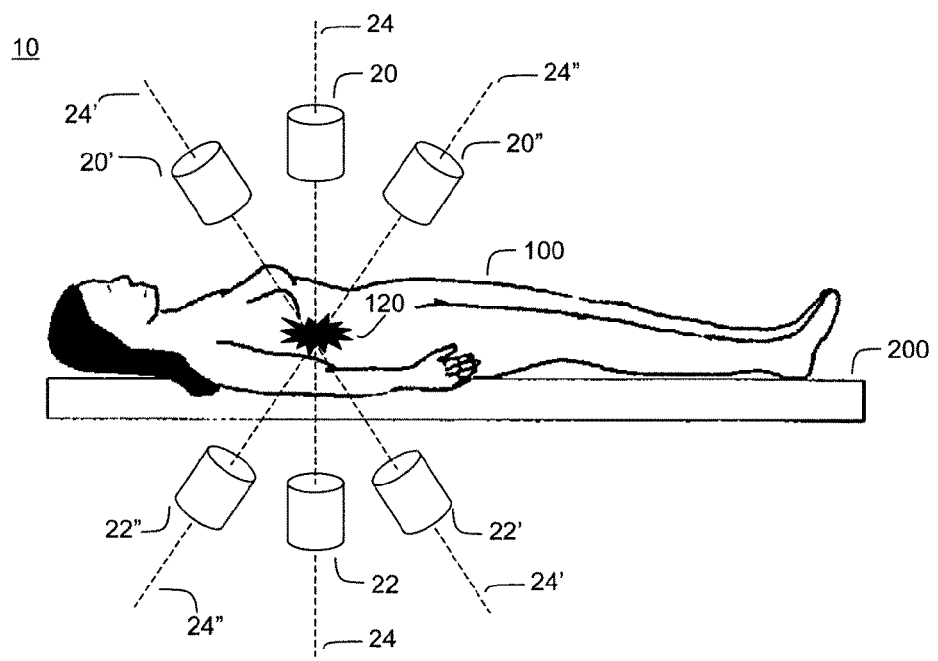
FIG. 2 is a schematic view of magnet orientation in a dynamic magnetic focusing treatment system according to an embodiment of the present invention.

Although FIG. 1 depicts only a single set of magnets, and a single sensing plane, it is understood that the systems of the preferred embodiments use multiple sets of opposing magnets. In a non-limiting example, six to ten magnets in total are used. The magnets are arranged in opposing sets, for example as depicted in FIG. 2, which shows six magnets 20, 20', 20", 22, 22', 22" arranged about the patient 100 so that the magnet axes 24, 24', 24" pass through the diseased material 120 but are separated enough from each other so as to maximize three-dimensional focusing of the magnetizable objects. For ease of illustration, FIG. 2 does not depict any of the components of system 10 other than the magnets.

Figure 3:
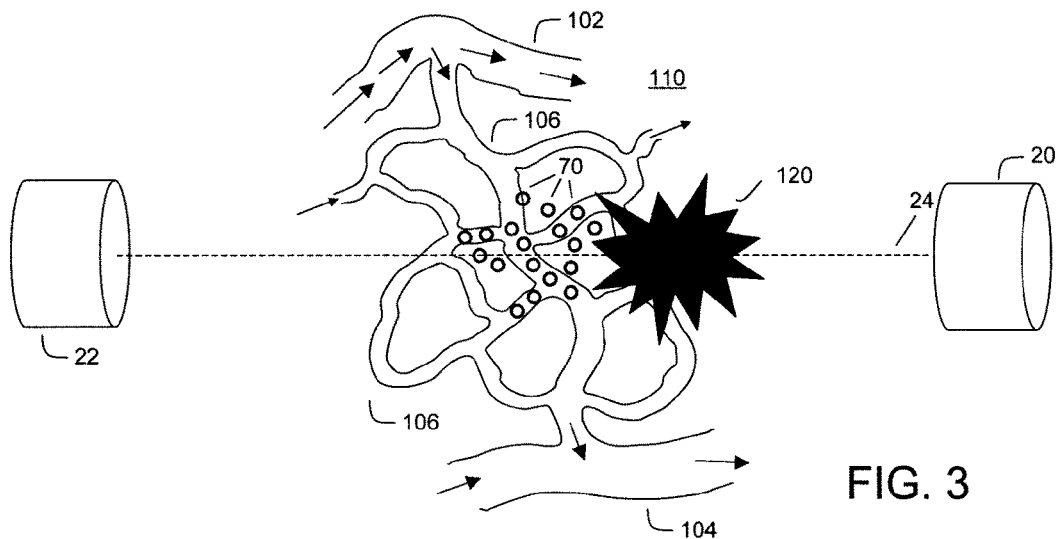
FIG. 3 is a schematic view of a dynamic magnetic focusing treatment system according to an embodiment of the present invention.

FIG. 3 depicts a dynamic magnetic focusing treatment of an embodiment of the present invention. A cut-away view of the patient's liver 110 and blood vessels including arteriole 102, venule 104, and capillaries 106 in the patient is shown, with arrows indicating the direction of blood flow. Magnetizable objects 70 are also shown in the capillaries 106 and the surrounding tissue near diseased material 120. For ease of illustration, only magnets 20, 22 and their magnetic axis 24 are shown here.

As can be seen, when first injected, the magnetizable objects 70 will be trapped by the magnetic forces at the regions of highest magnetic field, which occur along magnetic axis 24. However, the objects 70 may not be correctly oriented on magnetic axis 24 to achieve optimal treatment of diseased material 120. For example, FIG. 3 depicts the magnetizable objects 70 as clustered to the left of diseased material 120. Information regarding the position of the magnetizable objects is obtained by sensor system 60 and collected by feedback controller 40, which then directs the DMF generator 30 to change the magnetic field to focus the objects.

For example, in the situation depicted in FIG. 3, the position of the magnetizable objects 70 would be corrected by increasing the strength of the right magnet 20 relative to the strength of the left magnet 22, thereby focusing the magnetizable objects 70 to the right and into diseased material 120. The alteration of the magnet strength and the varying of the magnetic field is carried out in accordance with the positional feedback received from the sensor system in real-time or as close to it as possible, such that if the magnetizable objects begin to drift away from the target area, the appropriate set (or sets) of magnets are controlled to correct the object positions. This control is highly complex due to the need to focus a large number of independent magnetizable objects at the same time.

The pairs of magnets are spaced apart from each other such that the patient or the body part to be treated is be inserted between the magnets. For example, although FIGS. 1 and 2 depict the entire patient body in between the magnets, for certain applications it is contemplated that only a part of the patient, for example the patient's leg, might be inserted between the magnets. A focusing distance of 30 cm from each magnet is desirable because it enables a gap of 60 cm between magnets (more than half a meter), which should be sufficient to target deep tumors even in obese patients. To find how forces on the magnetizable objects scale with focusing distance, magnet dimensions and strength, Biot-Savart's law was integrated over a planar coil arrangement (as in the experiment of Example 1, coil radius a=3 cm, length L=1 cm)

to find the following solution for the magnetic field along the vertical magnet axis in Equation (2):

$$H_z(z) = \frac{\gamma}{2} \int_0^L \log\left(1 + \sqrt{((z+q)/a)^2 + 1}\right) - \qquad (2)$$
$$1/\sqrt{((z+q)/a)^2 + 1} - \log\left(\frac{z+q}{a}\right) dq = \frac{\gamma}{2} f(z/a)$$

where z is the distance from the magnet, $\gamma$ is the current density (units A/m$^2$) and f is a complex function defined by the integral (not shown). The on-axis magnetic force goes as $F_z \sim \partial(H_z^2)/\partial z$. Thus the magnetic force on the magnetic composition scales linearly with magnet size—doubling the size of the magnet doubles the focusing distance. Because the force goes as the magnetic field squared the scaling with respect to current density is better than linear—doubling the focusing distance requires increasing $\gamma$ by $\sqrt{2}$. Scaling up the magnet size to a radius of a=10 cm and a length of L=3 cm achieves the same focusing force as in the experiment of Example 1, but at a distance of 30 cm with a 1.5 Tesla electromagnet—well below the ~4 Tesla value used in high-strength MR imaging. Increasing the strength of the magnets to 4 Tesla will allow a focusing force 6.7 times greater, per each such magnet, at a distance of 30 cm. This is without optimizing the shape of the magnet (e.g., shaped cone instead of a squat cylindrical) which, based on initial calculations, will give another five-fold factor of improvement in focusing force, per magnet.

Although a dynamic magnetic field is used, changes in the magnetic field should not be made too rapidly in order to avoid undesirable physiological responses in the patient due to eddy currents. For example, rate of change (dB/dt) values of 60 Tesla/second are known to cause muscular twitches in the face and back along with uncomfortable "electric shock" sensations, hence the U.S. Food and Drug Administration ("FDA") has recommended that dB/dt not exceed 20 Tesla/second. Accordingly, although the embodiments of the present invention are not limited, it is preferred for use in medical applications with a living patient that the magnetic field be varied slowly at rates that are considered to be safe for medical use. In an embodiment of the present invention, the rate of change (dB/dt) is less than about 80 Tesla/second, and more preferably less than about 70, 60, 55, 50, 45, 40, 35, 30, 25, 20, 15, or 10 Tesla/second. In a different embodiment, the rate of change (dB/dt) is less than about 25, 24, 23, 22, 21, 20, 19, 18, 17, 16, 15, 14, 13, 12, 11, 10, 9, 8, 7, 6, 5, 4, 3, 2, or 1 Tesla/second.

Likewise, the strength of the magnetic field that can be used is not limited, but for medical applications is generally desired to be no greater than about 8 Tesla for adults and 4 Tesla for children. Accordingly, although a magnetic field of any strength could be used, it is preferred for use in medical applications with a living patient that the magnetic field strength be no greater than about 10 Tesla, and more preferably no greater than 9.5, 9, 8.5, 8, 7.5, 7, 6.5, 6, 5.5, 5, 4.5, 4, 3.5, 3, 2.5, 2, 1.5, 1, 0.75, 0.5, 0.25, or 0.1 Tesla. In a preferred embodiment, the field strength is no greater than 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 Tesla, and most preferably is less than about 1 Tesla. In a preferred embodiment, the rate of change is no greater than 20 Tesla/second, and a moderate field strength of 0.5 Tesla is used. This implies a bandwidth limitation of ≤40 Hz, although a weaker field can be traded for higher frequency.

B. Magnetizable Compositions

The magnetizable compositions of the present invention comprise multiple magnetizable objects, e.g., a plurality of magnetizable nano-particles, such a plurality of particles comprising, for example, a ferrofluid—a suspension of magnetizable particles forming a magnetizable fluid. As used herein, the term "magnetizable" refers to the capability to become magnetized, and includes within its scope magnetic, paramagnetic, ferrous and diamagnetic. The magnetizable objects may have any suitable shape and composition, and are limited only by the need for them to be magnetically responsive and small enough to transport in the vasculature. Because there are multiple magnetizable objects, it is more difficult to focus all or a substantial number of the objects in the body, because each object is capable of moving independently of the other objects. In various embodiments, the magnetizable objects comprise a therapeutic agent or a visualization agent, for therapeutic, prophylactic, and diagnostic uses.

The object size can be any size suitable for transport in living tissue or vasculature and capable of being focused magnetically. While larger objects are desirable to enhance magnetic manipulation (larger objects can be controlled with lower magnetic fields), objects over 250 nm in diameter may not be able to pass through cell pore membranes easily or at all. In a preferred embodiment, the objects are small enough in size (less than about 250 nm diameter) to be able to diffuse into tissue and then enter cells (e.g., via endocytotic processes), while still being large enough (greater than about 100 nm diameter) to respond to the applied magnetic field.

The force per-unit-volume on the objects can be calculated on an object-by-object basis as per Equation 1 discussed previously. As is evident from Equation 1, the force on a ferrofluid equals the object concentration times the object volume, times the gradient of the magnetic field squared. Therefore, it can be seen that bigger objects under stronger magnetic fields, with higher gradients, will be easier to capture, although upper limits on object size are created by safety limitations placed on the magnetic field strength and temporal frequency. Magnetic spatial field gradients are limited by the engineering capability of accurately creating magnetic fields.

In preferred embodiments, the magnetizable objects are nano-objects or micro-objects. As used herein, the term "micro-object" refers to an object that has an average diameter of about 1 to 1000 μm, and the term "nano-object" refers to an object that has an average diameter less than 1000 nm. In an embodiment of the present invention, the magnetizable objects have an average diameter in the range of about 1 nm to 1 mm, preferably in the range of about 100 nm to about 200 nm, about 300 nm, about 400 nm or about 500 nm, or in the range of about 200 nm to about 300 nm, about 400 nm or about 500 nm, or in the range of about 300 nm to about 400 nm or about 500 nm, or in the range of about 400 nm to about 500 nm.

In a different embodiment of the present invention, the magnetizable objects are micro-objects having an average diameter of less than about 250 μm, 200 μm, 150 μm, 100 μm, 75 μm, 50 μm, 25 μm, 20 μm, 15 μm, 10 μm, or 5 μm. In another embodiment, the magnetizable objects are nano-objects having an average diameter less than about 500 nm, 450 nm, 400 nm, 350 nm, 300 nm, 250 nm, 225 nm, 200 nm, 175 nm, 150 nm, 125 nm, 100 nm, 75 nm, 50 nm, 25 nm, 15 nm, 10 nm, 5 nm, or 1 nm. In yet another embodiment, the magnetizable objects are nano-objects having an average diameter in the range of about 1 to 500 nm, preferably in the range of about 25 to 400 nm, about 50 to 350 nm, about 60 to about 325 nm, about 75 to 300 nm, about 90 to 275 nm, about 100 to 250 nm, or about 125 to about 225 nm.

The magnetizable objects used in the methods of the present invention can be based on any biologically suitable material, and may take a variety of forms, such as liposomes, microspheres, nanospheres, micelles, vesicles, capsules, needles, or rods. The objects may be made out of any suitable biocompatible material such as chitosan, dextran, poly(lactic acid), starch, poly(vinyl alcohol), polyalkylcyanoacrylate, polyethylene imine, carbon, polysaccharides, heparin, gelatin, viral shells, and proteins. The magnetizable object may also be a cell that has been modified to contain or to be attached to a magnetizable material. The objects may have various coatings or attached substances, for example, a layer of carbohydrates may be attached to the objects in order to prevent aggregation (clumping) and a phosphate coating may be used to enhance in vivo residence time.

The magnetic responsiveness of the magnetizable objects may come from materials such as magnetite, iron, nickel, cobalt, neodymium-iron-boron, or samarium-cobalt, or any other material that reacts to a magnetic field. The magnetically responsive material may be biocompatible, may be biologically incompatible but coated with a biocompatible coating or layer, or may be non-biocompatible, for example a radioactive particle that is meant to cause tissue damage in order to effect radiotherapy in the patient. The magnetically responsive material may form an integral part of the object, for example a particle core or a nanorod coating, or may be attached to the object, for example attached to the surface of the object. In one embodiment, the magnetizable objects comprise magnetite ($Fe_3O_4$), which has a magnetic susceptibility ($\chi$) of about 20, which is 5-7 orders of magnitude higher than the magnetic susceptibility of the body. In a different embodiment, the object has a core of magnetizable material such as iron oxide coated with carbohydrates linked to a therapeutic agent, for example epirubicin, mitoxantrone, etoposide, or paclitaxel.

In a preferred embodiment, the magnetizable objects comprise a magnetically responsive core coated with a biocompatible material, which protects the magnetic material from the surrounding environment and can also facilitate functionalization by allowing the attachment of carboxyl groups, biotin, avidin, and other functional groups that can act as attachment points for therapeutic agents or targeting molecules.

In certain embodiments, the magnetizable objects are associated with a therapeutic agent (e.g., the therapeutic agent is entangled, embedded, incorporated, encapsulated, bound to the surface, or otherwise associated with the particle). In certain embodiments, the therapeutic agent is a drug such as a pure drug (e.g., drugs processed by crystallization or supercritical fluids), an encapsulated drug (e.g., polymers), a surface-associated drug (e.g., drugs that are adsorbed or bound to the object surface), or a complexed drug (e.g., drugs that are associated with the material used to form the object). In a different embodiment, the magnetizable objects exhibit fluorescent activity or a measurable signal when exposed to light or another external stimulus, which is useful for diagnostics, imaging and sensing.

The term "agent", as used herein, is thus intended to include compounds having utility for therapeutic and/or diagnostic and/or prophylactic purposes (e.g., therapeutic, diagnostic or prophylactic agents). The invention particularly relates to therapeutic agents. Therapeutic agents useful in the methods of the present invention include, but are not limited to, antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding (minor groove) compounds, hormones, vitamins, proteins, peptides, polypeptides and peptide-like therapeutic agents. Diagnostic agents include, for example, dyes, contrast agents, fluorescent agents, radioisotopes (e.g., $^{32}P$, $^{99}Tc$, $^{18}F$, $^{131}I$, etc.) and the like that are useful in the diagnosis of diseases, conditions, syndromes or symptoms thereof. A therapeutic agent administered in advance of the detection of a disease, condition, syndrome or symptom is a prophylactic agent.

The magnetizable composition may comprise a carrier fluid in addition to the magnetizable objects, for example an organic solvent or water, so that the magnetizable composition has the form of a ferrofluid. A ferrofluid, which is composed of many small magnetizable objects or particles, is effectively super-paramagnetic—it is strongly magnetized in the presence of an external field and is demagnetized as soon as the external field is removed due to rapid random particle reorientations.

C. Magnetism and the Body

Magnetic fields can be described using magnetostatic equations, such as Maxwell's Equations (3) (magnetostatic, as opposed to magnetodynamic, equations are appropriate even for the dynamic magnetic fields discussed herein, because the field varies slowly compared to the timescales on which electric and magnetic fields interact):

$$\nabla \cdot \vec{B}=0 \text{ and } \nabla \times \vec{H}=\vec{j}$$

where B is the magnetic field (magnetic induction) in Tesla, H is the magnetic field strength in Amperes/m, and j is the current density, in $A/m^2$. In a vacuum, $B=\mu_0 H$. In a material, $B=\mu_0(H+M)=\mu_0(H+\chi H)$ where M is the material magnetization. The human body consists of 80% water, along with other essentially non-magnetic materials (proteins, lipids, carbohydrates), and trace amounts of metals. As a result, magnetic fields are essentially unmodified as they pass through the body ($M_{body} \sim 0$; $\chi \sim^{-6}$ to $10^{-4}$). In this model, control will be fairly slow, and the magnetic field will be used to create a slow averaged trap at disease-location blood vessel walls, where the blood flow is slow due to wall viscous forces.

When injected, the magnetizable objects are conveyed by the blood stream, will undergo diffusion within the blood, and will be taken up and diffused through healthy and tumor cells inside the body. In humans, blood flows at up to 1.75 m/s in the ascending aorta, 40 to 70 cm/s in the cerebral arteries, and about 20 cm/s in main venus arteries. In secondary vessels including microvessels, which can be as small as 5 μm in diameter, blood velocity may be as high as 1 mm/s. In the blood vessels, the magnetizable objects will be carried along by the local blood flow velocity $V_{blood}$, with magnetic forces creating an additional velocity $V_r$ relative to the blood flow. This relative velocity is set by a competition between magnetic and drag forces on the particle. The Stokes drag on a spherical particle in a liquid is shown in Equation (4):

$$\vec{F}_{drag}=6\pi a \eta \vec{V}_r \quad (4)$$

where $\eta=0.003$ N s/m$^2$ is the viscosity of blood. Setting Equations 4 and 1 equal, but per-particle (no C in Equation 1), gives the velocity of a single particle relative to blood flow as Equation (5):

$$\vec{V}_r = \frac{2a^2}{9\eta}\mu_0 \frac{\chi}{1+\chi/3}\nabla(\vec{H}^2) \quad (5)$$

This relative velocity is reached when the magnetic force on a particle is balanced by the blood drag force. For a 250 nm diameter particle in a 0.5 Tesla/cm magnetic gradient, this relative velocity will be $|V_r|\sim 30\times 10^{-6}$ m/s=30 μm/s, which is small compared to the ~1 mm/s blood flow velocity seen in secondary and micro arteries, but still strong enough for the magnetic forces to hold the objects against the blood flow. One reason for this is that blood flow is fast near the center of arteries, but slows to almost zero at the blood vessel walls. In macro vessels (>50 μm in diameter), blood acts essentially as a Newtonian fluid, having a roughly parabolic flow profile with maximum velocity at the center and zero velocity at the walls. Objects near the boundaries of the vessel see low blood flow velocities and can be captured by magnetic forces. Assuming such a parabolic flow profile and equating the maximum forces of Equation 1 versus the velocity dependent drag forces of Equation 4, the thickness of the magnetizable object capture region can be estimated. For a 1 mm diameter secondary blood vessel with a high 1 mm/s blood flow velocity, 250 nm diameter particles in a 0.5 T/cm magnetic gradient will be captured to a depth of ~7 μm. Hence, magnetizable objects are being concentrated in a thin layer at the blood vessel walls, which is highly desirable because the objects can then enter into vessel wall cells and migrate under the magnetic field to interior tissue cells.

Based on the above, the approximate governing partial differential equations for magnetizable object transport in blood vasculature are Equation (6):

$$\frac{\partial C}{\partial t} = -\nabla\cdot\left(-D\nabla C + \vec{V}C\right) \quad (6)$$

$$\vec{V} = \vec{V}_{blood} + \vec{V}_r = \vec{V}_{blood} + \frac{2a^2}{9\eta}\mu_0\frac{\chi}{1+\chi/3}\vec{M}_{sat}\cdot\nabla\vec{H}$$

Here $C(x, t)$ is the concentration of the magnetizable objects in 3D space and time [in number of moles/m³], D is the diffusion coefficient for objects in blood (small, probably negligible), V is the velocity of objects and is the sum of the local velocity of the blood $V_{blood}$ (large, pulsatile, varies in space and time) and the velocity $V_r$ due to the magnetic field gradient is as in Equation 5. This PDE is defined over a blood vasculature domain. As discussed, only near the blood vessel walls is $V_r$ comparable to $V_{blood}$, and so this is the region where the control must concentrate the objects.

After being concentrated at the vessel walls in the vicinity of the tumor, the magnetizable objects are absorbed by the vessel wall cells. The mechanisms are not known in detail. Tumor cells generally have more porous membranes that can take up larger objects than non-tumor cells, but it is also known that cells can eject objects after having taken them up. Once the magnetizable objects are inside the cells, they will drift under the applied magnetic field, moving from cell to cell or between cells. Because every cell in the body is within about 100 μm of a blood vessel (about 5-20 cells distance), the remaining distance that must be covered by the magnetizable objects, from the blood vessel to the farthest tumor cells, is small.

The in-tissue analog of Equation 6 for magnetizable object transport through cells surrounding the blood vessels is Equation (7):

$$\frac{\partial C}{\partial t} = -\nabla\cdot\left(-D\nabla C + \vec{V}C\right) \quad (7)$$

$$\vec{V} = k\mu_0\vec{M}_{sat}\cdot\nabla\vec{H}$$

where k is the mobility coefficient for magnetizable objects through tissue (from cell to cell and between cells). This PDE is defined over the tissue surrounding a blood vasculature domain. Here, outside the blood vessels, the magnetic field forces no longer need to compete against large blood forces, but instead compete mainly against diffusion.

Applying these principles to the systems and methods of the present invention, it is evident that a magnetic field may be dynamically manipulated in order to focus magnetizable objects to particular regions in a patient's body, even deep targets within the body such as the lungs, intestines, or liver. In preferred embodiments, the focusing target is at least 5 cm, 10 cm, 15 cm, 20 cm, 25 cm, or more than 30 cm within the body. As is evident from the foregoing discussion, the focusing of the objects can be evaluated either at an instant in time, or on average over a time period.

It is also understood that the focusing of magnetizable objects is a relative achievement, and that 100 percent of the administered objects need not be focused in order for the methods and systems to effectively treat a patient. Conventional methods of administering chemotherapy currently deliver less than about 0.1 percent of chemotherapeutic agents to the diseased tissue. In a preferred embodiment, at least 0.1 percent, 1 percent, 5 percent, 10 percent, 50 percent, or 95 percent of the administered magnetizable objects are focused on the diseased material to be treated. In a different preferred embodiment, the focusing of the administered magnetizable objects results in delivering more chemotherapeutic agents to the diseased tissue than in conventional chemotherapeutic methods, e.g., focusing 1.1 times the standard amount (about 0.1 percent) of chemotherapeutic agents to the diseased tissue, or focusing 1.5 times, 2 times, 3 times, 4 times, 5 times, 6 times, 7 times, 8 times, 9 times, 10 times, 100 times, 1000 times, or more than 1000 times the standard amount to the diseased tissue.

D. Feedback Control Algorithm Design

Feedback control in the systems and methods of the present invention is governed by a control algorithm, which decides what magnet to actuate when and for how long in order to focus the magnetizable objects in the body. Control is complicated because inside a patient many factors are unknown (such as his/her vascular geometry, blood flow, and rates of object uptake from blood to tissue) but some factors are known. The magnetic fields applied to the body are known, as are the magnetic forces that they generate on the magnetizable objects. Any suitable control algorithms may be used to control feedback.

Non-limiting examples of control algorithms used in a preferred embodiment are based on the mathematical model of Equation (8):

$$\frac{\partial}{\partial t}C(\vec{r}, t) = -\nabla\cdot \quad (8)$$

$$\left[C(\vec{r}, t)\vec{V}_{blood}(\vec{r}, t) - D(\vec{r})\nabla C(\vec{r}, t) + k(\vec{r})C(\vec{r}, t)\nabla\left(|\vec{H}(\vec{r}, t)|^2\right)\right]$$

Here, C is the concentration of nanoparticles in the body as a function of time t and space $r=(x, y, z)$. C can be measured using a sensor system as previously described, for example a gamma ray camera. It should be noted that although the following discussion refers to nanoparticles, the invention is not so limited. $V_{blood}$ is the blood convection, D is the diffusion, k is the magnetic drift coefficient, and $\nabla(|H|^2)$ is the control.

The rate of change of the nanoparticle concentration is given by the gradient $\nabla$ of the flux. The flux is composed of 3 terms. First, transport of particles by the blood flow velocity $V_{blood}$. The velocity of blood is high in some regions, it varies from person to person, is pulsatile, and currently it is not feasible to measure it for each patient. Second, in addition to being carried by the blood, the nanoparticles diffuse within the blood stream. For spherical nanoparticles in blood at body temperature, Brownian diffusion can be calculated by Einstein's law, but red blood cell collisions may further scatter the particles and this scattering can be modeled as additional diffusion. The effect is greatest at the blood vessel walls where the blood shear is highest and it makes the diffusion coefficient D a patient-specific function of space r. Third, the applied magnetic field creates a velocity of the nanoparticles relative to the blood flow, a magnetic drift. Its size is determined by the balance between the applied magnetic force and the opposing viscous forces (Stokes drag) in the blood. The resulting coefficient is $k=(a^2/9\eta)\,\mu_0\chi(1+\chi/3)$ where $\eta$ is the viscosity of blood and a, $\mu_0$, and $\chi$ are as defined for Equation 1. However, blood Stokes drag on a spherical particle increases when it is near the blood vessel wall due to edge effects and this makes k a function of space. Magnetic fields are essentially unaffected by tissue and so the $\nabla H^2$ term is known precisely, even inside the body. Here the convection, diffusion, and magnetic drift of the nanoparticles occurs inside a vasculature network geometry, which varies greatly from person to person.

It is likely that patient to patient vascular geometry variation does not have an enduring impact in the following sense. All metabolically active cells are within <100 μm of a blood vessel, and for any given patient there is enough vessel connectivity to allow the nanoparticles to move from one millimeter sized location to its neighbor. Therefore, a control algorithm that operates for representative vasculatures will work for other vasculatures as well. However, a standard control algorithm is not required to practice the methods and systems of the present invention. Patient-to-patient variation may be accounted for in the control algorithm, for example by measuring individualized blood flow velocities, or mapping individual vasculature geometries, and therefore control algorithms can be selected, or customized, for specific locations within a patient (e.g. for lung vs. head and neck targeting) or for individual patients or groups of patients.

The control goal is to manipulate the last term of Equation 8 to correct for nanoparticle location errors caused by the diffusion term and the blood convection terms in the smaller blood vessels. It is not possible to correct for blood flow forces at the center of main arteries and veins, the flow there is too strong. Our control algorithm uses this third term to increase particle concentration at the deep tumor location whenever possible: it does not require knowledge of blood vasculature geometry or blood flow distribution in each patient.

An optimization problem whose solution will determine the magnetic field that is applied to focus the nanoparticles at each moment in time is now defined. If the deep tumor target is located at position $\vec{r}^*=(x^*,y^*,z^*)$ in the patient's body, then the degree of nanoparticle targeting achieved at time t is quantified by the cost, as shown in Equation (9):

$$J(t) = -\int C(\vec{r},t) W(\vec{r},\vec{r}^*) d\vec{r} \qquad (9)$$

where C is the concentration of the nanoparticles, W is a weight that is large at the tumor and small elsewhere, and the integral is over a body volume that contains the tumor target. This cost J is high if the nanoparticles are concentrated near $(x^*,y^*,z^*)$ and is small otherwise. The weight W can also reflect a tumor shape or region, instead of a point, the mathematics remains the same. The control goal is to maximize the cost J.

Differentiating Equation 9, and using Equation 8, the time rate of change of this cost is given by Equation (10):

$$\frac{\partial J}{\partial t} = \int \frac{\partial C}{\partial t} W d\vec{r} = \int [-\nabla \cdot (C\vec{V}_{blood}) + \nabla \cdot (D\nabla C)] W d\vec{r} - k\int [\nabla C \cdot \nabla \vec{H}^2 + C\nabla^2 \vec{H}^2] W d\vec{r} \qquad (10)$$

Here the integral has been split, the chain rule was used on the control term, and k was treated as constant. The last 2 terms correct for nanoparticle position errors cased by the first two terms, diffusion and blood convection, on the right hand side.

Thus H must be optimally chosen to best focus all, or a majority of or a fraction of, the nanoparticles. Using a few (N=10) stationary electromagnets whose strength can be dynamically controlled. When at unit strength, the jth magnet will create a magnetic field $H_j(r)$. By the linearity of Maxwell's equations (3), if at time t all N magnets are actuated at strengths $u(t)=[u_1(t), u_2(t), \ldots, u_N(t)]$, then the net resulting magnetic field is calculated by Equation (11):

$$\vec{H}(\vec{r},t) = \sum_{j=1}^{N} u_j(t) \vec{H}_j(\vec{r}) \qquad (11)$$

Substituting 11 into 10, expanding the square, and rearranging the integral yields Equation (12):

$$\frac{\partial J}{\partial t} = \int [-\nabla \cdot (C\vec{V}_{blood}) + \nabla \cdot (D\nabla C)] W d\vec{r} - k\int W\nabla C \cdot \nabla\left(\sum u_j \vec{H}_j\right)^2 + WC\nabla^2\left(\sum u_j \vec{H}_j\right)^2 d\vec{r} =$$

$$\ldots -k\sum_{i=1}^{N}\sum_{j=1}^{N} u_i \left[\underbrace{\int W\nabla C \cdot \nabla(\vec{H}_i \cdot \vec{H}_j) d\vec{r}}_{A_{ij}} + \underbrace{\int WC\Delta^2(\vec{H}_i \cdot \vec{H}_j) d\vec{r}}_{B_{ij}}\right] u_j = \ldots -k\vec{u}^T[A+B]\vec{u} \qquad (12)$$

In the second line only the control term is written, the other terms are marked by dots. In the second line, $A_{ij}$ is the first integral in the brackets, and $B_{ij}$ is the second. The matrices A and B, with integral entries $A_{ij}$, $B_{ij}$, can be quickly computed at each new time (only C changes): the weight W was chosen, nanoparticle concentration C is being measured, and the magnetic fields $H_i$ and $H_j$ are accurately known from simulation. The control $u(t)=[u_1(t), u_2(t), \ldots, u_N(t)]$ makes $-ku^T[A+B]u$ as positive as possible so that it increases focusing metric J as much as possible.

Safety constraints can be imposed on the magnetic fields as hard bounds (no control action will exceed them). For example, from Equation 11, using a 4 Tesla limit for children, a quadratic constraint on the control action u is given by Equation (13):

$$|\vec{H}|^2 = \vec{H}(\vec{x},t) \cdot \vec{H}(\vec{x},t) = \Sigma\Sigma u_i u_j \vec{H}_i \cdot \vec{H}_j \leq (4T/\mu_0)^2 \qquad (13)$$

Likewise, the FDA safety limit on the rate of change (20 T/s) can be used as another quadratic constraint on the change in control, which, from the prior known value of the control translates into a quadratic constraint on u. These limits on magnetic field strength and rate of change will still allow deep tissue (~30 cm) focusing. Nanoparticles are being focused primarily in micro-capillaries and at vessel walls where the blood velocity is slow, so extremely fast magnetic field actuation is not required. This constraint still allows a strong, say 3 T, stationary baseline field with significant on-top modulation of ±1 T at 20 Hz—a strong modulation 20 times faster than the resting heart rate. Finally, tissue specific absorption rates (SAR) are not a safety issue because the dynamic magnetic field is modulated at tens of Hz, orders-of-magnitude below radio-frequencies, and therefore will not cause any appreciable SAR heating.

Maximization of deep nanoparticle focusing—$ku^T[A+B]u$ is thus, in this preferred embodiment, a quadratic cost problem with quadratic constraints. This is a standard optimization problem, in this case a small problem (its dimension is equal to the number of electromagnets, $N \leq 10$), and it can be solved quickly (between control updates). The focusing metric is improved whenever the optimal control term can focus the nanoparticles more than the diffusion and convection terms defocus them. This control algorithm does not require measurement or knowledge of patient-specific vasculature geometry or blood flow velocities. Whenever it is possible to improve the concentration of nanoparticles at the deep tumor target by choosing a magnetic field, this optimization will do so.

Having now generally described the invention, the same will be more readily understood through reference to the following examples, which are provided by way of illustration and are not intended to be limiting of the present invention unless specified.

Example 1

Focusing of a Ferrofluid in Air

Three-dimensional focusing of magnetizable particles in blood was modeled using a ferrofluid in air. A droplet of ferrofluid was focused to a target 1 cm away from an electromagnet using infrared sensing and electromagnetic feedback control in air, using a dynamic 0.02 Tesla magnetic field.

Large (5-8 mm) drops of magnetic liquid were suspended against gravity using an actively controlled magnetic field gradient. The drop was freely suspended in air, but its equilibrium shape depended mainly on the value of the magnetic field, with a small correction for the influence of the magnetic gradient across the dimension of the drop. The dynamics of the ferrofluid were described by Equation 1 and by surface tension forces on the droplet. Surface tension was ignored and the control algorithm was designed by shaping the applied magnetic field strength H (equivalently magnetic field B). According to Equation 3, it is not possible to have a magnetic field that increases in all three spatial dimensions simultaneously and whose gradient therefore points inwards from all directions, so the practical implementation requires a coil arrangement designed to confine the drop in the horizontal plane, with vertical stability achieved via an active feedback system.

Figure 4:
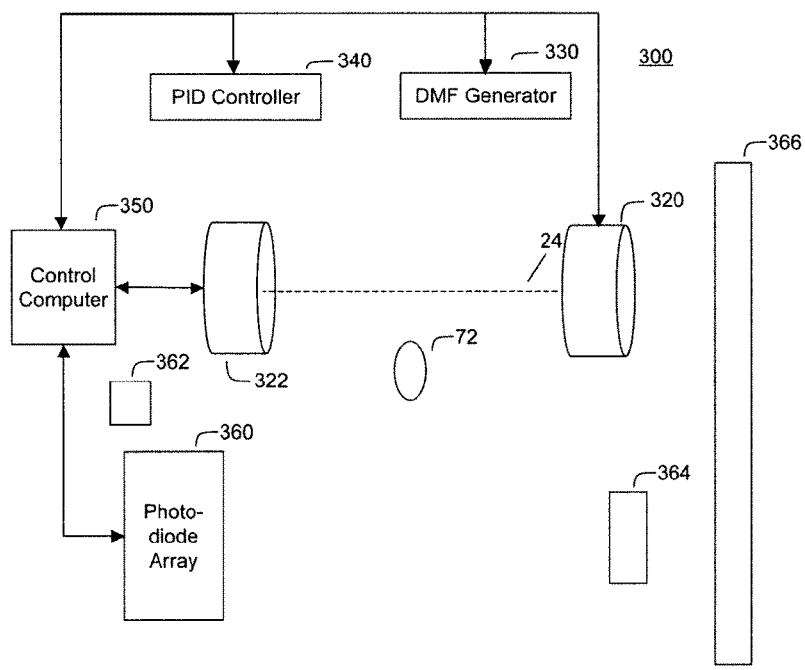
FIG. 4 is a schematic view of an experimental apparatus used to focus a droplet of ferrofluid in air.

FIG. 4 depicts the experimental set-up 300 including a magnetic coil (shown here as coil ends 320, 322), which under the control of DMF generator 330 creates a maximum magnetic field strength at its center, along the vertical axis of drop 72. Focusing to this axis, in two dimensions, is passive. Along the axis, gravity acts down and magnetic forces act up. The resulting equilibrium point is a function of the electromagnet strength, and is a saddle—it is stable in the horizontal plane and unstable in the vertical plane. A proportional-integral-derivative (PID) controller 340 is used to stabilize the vertical direction.

Information on the drop position was obtained from a linear array 360 of sixteen photodiodes with a spacing of 1 mm. The array 360 measured the shadow cast by the suspended drop 72 from a diffuse infrared linear light source 364. A shadow is also cast by the drop 72 on glass screen 366 by means of point light source 362. The output from the photodiodes 360 was interfaced directly to the control computer 350 by a 16 channel, 12 bit A/D card (Amplicon PCI230). Each channel was read nearly simultaneously at a 1 kHz sample rate. Because the shadow was diffuse, a curve could be fitted to all the data points, giving the drop vertical position with an accuracy of about 0.1 mm, and the drop vertical axis length to within 0.2 mm. To stabilize the drop in the vertical direction the data on drop position was fed into a software implemented PID controller 340 which set the current fed to the coil of the levitation magnet 320, 322.

Typical field strengths were around 0.02 Tesla. A drop of ferrofluid was launched from a syringe into the apparatus, where the PID controller detected it, and adjusted the field to catch and hold it. The volume of the drop dispensed was controlled by the diameter of the needle (0.5-1 mm diameter) for small drops, and by the size of the collar fitted to the needle (2-4 mm) for larger drops. It was possible to generate very large drops (>10 mm long) by injecting extra ferrofluid into a suspended drop, but drops this large were hard to stabilize as they tended to split into two smaller drops if disturbed.

FIG. 4 shows a suspended ferrofluid drop that is elliptical in cross-section. It shows that it is possible to trap the ferrofluid to a target in 3D space by passive focusing in two dimensions (here, a horizontal plane) and active control in the remaining dimension (here, along the vertical axis).

Example 2

Saddle Motion Control at Blood Vessel Walls

The methods used to focus the ferrofluid in air, will be applied to achieving the same type of focusing in a complex blood vasculature geometry, in the presence of large perturbing forces from pulsatile blood flow.

FIG. 3 illustrates the saddle motion control of ferrofluid in a blood vasculature network. The magnetic field is strongest along the magnet axis 24 and the ferrofluid will flow to this axis along the inside of blood vessel walls. Once near the axis, the particles will flow toward the nearest or strongest magnet. By varying magnet strength and positioning the saddle on either side of the majority of the ferrofluid, the ferrofluid can be shuttled between magnets to focus, on average, to the tumor location 120.

Focusing in the two dimensions perpendicular to the axis between the magnets is passive: the highest magnetic field is along the axis and so the magnetic forces point in toward the centerline. These passive forces will move the particles toward this axis along the inside blood vessel walls irrespective of the precise shape of the vasculature network. There is enough connectivity and orientation directions in blood vasculature network to allow the ferrofluid to continuously find a path closer to this axis. Still, it is possible and likely that the particles will get caught in local minima—and this cannot yet be quantified to what degree this will happen. A potential solution is to swivel the magnet axis to move the ferrofluid out of local pockets.

To control the ferrofluid along the magnet axis, the strength of the two opposing magnets will be slowly changed to position the saddle equilibrium point on one side or the other of the majority of the ferrofluid, to continuously move it back toward the tumor, as shown in FIG. 3. For example, if the ferrofluid center-of-mass along the magnet axis is to the left of the tumor, magnet strengths will be chosen to position the saddle to the left of this ferrofluid center (left magnet weak, right magnet strong), which will push fluid back right toward the right magnet and tumor along the complex topology of the inside surface of the vasculature network. This is the same idea as applied in Example 1, but now over a network geometry and against varying blood flow drag instead of a constant gravity force.

Example 3

Electromagnet Control and Sensing

The ability to control and sense magnetizable nanoparticles in a ferrofluid at distances greater than 30 cm will be confirmed via the following procedure. The required stronger (~1.5 Tesla) magnets will be custom made from microbore copper piping (to allow in-situ water cooling) wound onto an appropriate core. The magnets will be driven by high-quality high-current kW power suppliers and amplifiers. A quiescent blood-mimic fluid such as that described by K. V. Ramnarine et al. (1998) Ultrasound in Medicine & Biology 24:451-459 (85% distilled water, 10% glycerol, 5% other additives) will be inside a clear 0.5 m on a side cubic container placed between sets of electromagnets. More than one magnet is needed to combat diffusion and buoyancy forces. A commercially available ferrofluid from Chemicell (Berlin, Germany) will be used that is composed of 250 nm diameter magnetizable particles.

Two, then six electromagnets, spaced 0.6 m apart, will be dynamically controlled to focus the ferrofluid. Focusing will occur on the magnet axis to any desired vertical location, such that the ferrofluid concentration is increased 100:1 as compared to background in a <1 cm diameter target region. The location of the ferrofluid inside this vessel will be imaged in real-time by two (or three) orthogonal cameras. A suitably fast frame-grabber will gather images from all the cameras at once, and in-house imaging algorithms will then be used to infer the position of the ferrofluid. If the applied magnetic field adversely impacts the function of the cameras (unlikely), then the cameras can be shielded or can be fed by optical fibers (so optics to fibers to camera imaging hardware) so that the cameras are completely protected.

The simple but successful proportional-integral-derivative (PID) control algorithm of Example 1 will be implemented to focus the ferrofluid at a distance of 30 cm. To do this, the electromagnets will be scaled up, as previously described, and the magnet design (size, shape, cores, amplifiers) will be optimized based on numerical simulations and optimization tools. After success with PID control, more advanced control schemes will be validated.

Example 4

Electromagnet Control and Sensing in 3D Vasculature Models

During treatment, drug-coated nanoparticles are injected into a vein. Hence deep tissue focusing must first be achieved within the vasculature, before extravasation in the target vicinity, diffusion and magnetic drift (intra and extra cellular), and cell uptake can deliver a portion of the focused chemotherapy drugs to tumor cells.

Blood flow carries the nanoparticles along and the magnetic field is used to stop and concentrate them. Even with a high magnetic field gradient, the magnetic forces are small compared to blood convection (particle drag) forces in major vessels. Only those particles in slow moving blood can be stopped. For example, for 250 nm particles with a moderate 1 T/cm magnetic field gradient at the target location, the particles can be stopped if the surrounding blood flow is <0.12 mm/s. Inside the body, blood flow velocities range from the very high (>1 m/s highest peak velocity in the ascending aorta) to ~30 cm/s in main blood return venus arteries to <5 mm/s in capillaries and venules. Yet 1 T/cm magnetic field gradients can capture and effectively concentrate particles, because the flow profile of blood in vessels is approximately parabolic, i.e., it is maximum at the vessel centerline and is low at the vessel walls due to viscous shear forces. Magnetic forces are strong enough to capture the nanoparticles in a thin boundary layer at the surface of minor blood vessels where the blood flow velocity is low. It is this thin, slow moving, coating of ferrofluid at the inside surface of the vasculature that must be controlled and concentrated.

To achieve these goals, the container of Example 3 will be replaced by a series of vasculature phantoms. Blood-mimic flow in these phantoms will be driven by a heart mimic pump (Shelley Medical Systems, London, Ontario). The electromagnet control algorithm, which will describe how to actuate the magnets so that they focus the ferrofluid inside the vasculature network, is based on the mathematical models previously described, with reference to Equation 8. The phantoms will use the blood-mimic fluid described by K. V. Ramnarine et al. (1998) Ultrasound in Medicine & Biology 24:451-459 (85% distilled water, 10% glycerol, 5% other additives) because it has the same approximate viscosity and density as blood. A heart pump mimic (Shelley Medical Systems) will drive the fluid.

The cameras will locate the position and shape of the ferrofluid inside the transparent vasculature phantoms, in real-time. Each camera will first take a photograph of the experimental setup without any of the ferrofluid. During the experiment, these nominal images will be subtracted away from the current images, thus identifying only those pixels that have changed—the ferrofluid. Real-time filtering, smoothing, and registration algorithms will be created to identify the location and shape of the ferrofluid in the phantom, as described by M. Armani et al. (2005) Int'l J. of Robust & Nonlinear Control 15:785-803 and I. Triese et al. (2004) Lab on a Chip 5:285-297. Image darkness correlates to local ferrofluid concentration. Light intensity will be measured against ferrofluid concentration, for a range of well-mixed ferrofluid concentrations in blood-mimic fluid under controlled light conditions, to provide a diagnostic curve of concentration vs. intensity. This curve will then be used to quantify the amount of ferrofluid focusing achieved during feedback control experiments.

Vasculature phantoms will proceed from simple to more advanced. The first phantom will be a transparent porous PDMS network. Polydimethylsiloxane is a clear plastic whose porosity can be controlled by preparation. Other transparent gels or plastics with different network properties can also be used. The purpose in this first 'phantom' is simply to introduce a network, so that ferrofluid focusing can be tested inside it. Magnets of ~2 T spaced 0.6 m apart will be used, with a ferrofluid comprising 250 nm diameter particles. Focusing will occur such that the ferrofluid concentration is increased 100:1 as compared to background in a <1 cm diameter target region. The blood mimic fluid is quiescent in this phantom.

The next phantom will be a more accurate representation of human vasculature. It is possible to fabricate phantoms from computer representations of vasculature, for example as described by C. P. Renaudin et al. (1994) Radiology 190(2): 579-582 and Y. Zhang et al. (2007) Computer Methods in Applied Mechanics and Engineering. Here, a computer aided manufacturing technique (e.g., stereolithography) is used to make a copy in plastic of a computer representation of the vasculature, as derived from MR imaging or the visible human project. Phantom resolution is set by the accuracy of measuring the vessels (e.g., the 1 mm spacing of slices in the visible human project), the resolution of the computer drawing reconstruction, and the spatial resolution of the fabrication process. Phantoms that will replicate human vasculature to ~1 mm accuracy are achievable using these methods. Six to 10 electromagnets (each ~2 Tesla), spaced 0.6 m apart, will focus 250 nm particles inside the phantom. With the blood mimic fluid quiescent, focusing will occur such that the ferrofluid concentration is increased 50:1 as compared to background in a region <2 cm in diameter. The heart-pump will also be used to mimic various physiological conditions of blood flow, under which conditions focusing will occur such that the ferrofluid concentration is increased 25:1 as compared to background in a region <2 cm in diameter.

The third phantom will be an inverse mold from real-body plastination specimens, which has the advantages of having micro-capillaries, in addition to the major veins and arteries above. Inverse molds of vasculature specimens that include micro-capillaries will be created using molds around the specimens, and then dissolving them out with acid. The result will be a mold that is clear plastic where tissue was and air where blood was. Different representative vasculatures will be used, beginning with head and neck vasculatures. Six to 10 electromagnets (each ~2 Tesla), spaced 0.6 m apart, will focus 250 nm particles inside the phantom with the heart-pump used to mimic various physiological conditions of blood flow, under which conditions focusing will occur such that the ferrofluid concentration is increased 25:1 as compared to background in a region <2 cm in diameter.

Example 5

Dynamic Control of Magnetic Fields Focusing Magnetic Carriers to Targets Deep inside The Body Background In magnetic drug delivery, magnetically-responsive objects coated by or containing therapeutic agents are injected into the blood and are then focused to targets in the body by applied magnetic fields. This approach is useful for the treatment of cancer, stroke, infection and other diseases because it allows the therapy to be concentrated to disease sites (solid tumors, blood clots, infections) while keeping systemic concentrations low (thus minimizing side effects). The magnetically-responsive objects are preferably micro- or nano-scale iron oxide or other particles coated appropriately to be bio-compatible and therapeutically effective, with sub-micron particles being small enough to pass from the blood to the surrounding tissue through blood vessel walls (with this extravasation generally taking place more readily through the leakier blood vessel walls of tumor vasculature). Other objects besides particles, such as polymer, microsphere, micelle, and nano-capsule delivery systems, can also be made magnetic or attached to magnetic particles and then used as magnetic carriers.

A limitation in prior magnetic drug delivery efforts lay in the inability to focus treatment to targets deep inside the body. When stationary external magnets are used they attract the particles and can only concentrate them near the skin surface—magnets of a maximum safe strength can only create a <5 cm deep focus (Voltairas, P. A. et al. (2002) "*Hydrodynamics Of Magnetic Drug Targeting*," Journal of Biomechanics, 35: 813-821; Grief, A. D. et al. (2005) "*Mathematical Modelling Of Magnetically Targeted Drug Delivery*," J. of Magnetism and Magnetic Materials, 293:455-463; Hafeli, U. O. et al. (2007) "*Modeling Of Magnetic Bandages For Drug Targeting: Button vs. Halbach Arrays*," J. of Magnetism and Magnetic Materials, 311:323-329). This is a well-known and well-recognized problem. It is a fundamental consequence of the classic Samuel Earnshaw 1842 theorem (Earnshaw, S. (1842) "*On The Nature Of The Molecular Forces Which Regulate The Constitution Of The Luminiferous Ether*," Trans. Camb. Phil. Soc., 7:97-112). This theorem states that no inverse-square law force (which includes magnetic forces on a single particle) can create a stable trap in the interior. With a static magnetic field, only unstable equilibria are possible for a ferro- or para-magnetic particle.

Earnshaw's theorem can be bypassed in three ways. First, magnets or magnetic materials, such as magnetic stents or magnetizable wires or needles, can be implanted inside the body to create a local magnetic field maximum and attract particles to them (Iacob, G. H. et al. (2004) "*A Possibility For Local Targeting Of Magnetic Carriers*," J. Optoelectronics and Advanced Materials 6:713-717; Ritter, J. A. et al. (2003) Abstracts of Papers of the American Chemical Society 225 (2003) U991; Iacob, G. H. et al. (2004) "*Magnetizable Needles And Wires—Modeling An Efficient Way To Target Magnetic Microspheres in vivo*," Biorheology 41:599-612; Avilés, M. O. et al. (2005) "*Theoretical Analysis Of A Transdermal Ferromagnetic Implant For Retention Of Magnetic Drug Carrier Particles*," J. Magnetism and Magnetic Materials 293:605-615; Rosengart, A. J. et al. (2005) "*Magnetizable Implants And Functionalized Magnetic Carriers: A Novel Approach For Noninvasive Yet Targeted Drug Delivery*," J. Magnetism and Magnetic Materials 293:633-638; Rotariu, O. et al. (2005) "*Modelling Magnetic Carrier Particle Targeting In The Tumor Microvasculature For Cancer Treatment*," J. Magnetism and Magnetic Materials, 293:639-647; Yellen, B. B. et al. (2005) "*Targeted Drug Delivery To Magnetic Implants For Therapeutic Applications*," J. Magnetism and Magnetic Materials, 293:647-654). Surgically implanting such objects in a patient can be undesirable and is not always possible in a clinical setting. Second, the walls of a container can hold particles away from a magnet: a magnet can trap magnetic carriers against a perpendicular confining wall. But the human blood vasculature network is not a collection of simple, conveniently oriented, confining vessels and, as we see in the animal and human clinical trials of our collaborator (Lubbe, A. S. et al. (1996) "*Preclinical Experiences With Magnetic Drug Targeting: Tolerance And Efficacy*," Cancer Res., 56:4694-4701; Lubbe, A. S. et al. (1996) "*Clinical Experiences With Magnetic Drag Targeting: A Phase I Study With 4'-Epidoxorubicin In 14 Patients With Advanced Solid Tumors*," Cancer Res., 56:4686-4693; Lemke, M. I. et al., (2004) "*MRI After Magnetic Drug Targeting In Patients With Advanced Solid Malignant Tumors*," Eur. Radiology, 14:1949-1955), magnetic carriers spill out from one blood vessel to the next to collect at vessels closest to the external magnet. A final way to bypass the theorem is to change the applied magnetic fields in time, and this is the approach of the present invention: to dynamically manipulate magnetic fields to focus magnetic carriers to deep targets.

The work of Potts and Diver (Potts, H. E. et al. (2001) "*Dynamics Of Freely-Suspended Drops*," J. of Physics D-Applied Physics, 34:2629-2636), shows that dynamic control of just a single electro-magnet can bypass Earnshaw's theorem: it can hold a drop of ferrofluid (nano-particles in suspension) at a distance from the magnet. The drop is held together by surface tension so the control is effectively that of a single object: if the drop is too low it is brought back up and vice-versa. Magnetic manipulation of single objects in-vivo by feedback control has been demonstrated by Martel, who has shown steering of one micro particle at a time in swine vasculature using an MRI machine (Martel, S. et al. (2007) "*Automatic Navigation Of An Untethered Device In The Artery Of A Living Animal Using A Conventional Clinical Magnetic Resonance Imaging System*," Applied Physics Letters 90:114105; Mathieu, J. B. et al. (2007) "*Magnetic Microparticle Steering Within the Constraints of an MRI System: Proof of Concept of a Novel Targeting Approach*," Biomedical Microdevices, 9:801-808), and by the company Stereotaxis who precisely controls magnetic fields to help guide surgical tools for magnetically assisted surgery (Ritter, R. C. (U.S. Pat. No. 6,241,671)) their instruments have achieved >10,000 successful heart surgeries.

During existing magnetic chemotherapy treatment, which has gone through phase I human trials for shallow tumors (Lubbe, A. S. et al. (1996) "*Clinical Experiences With Magnetic Drag Targeting: A Phase I Study With 4'-Epidoxorubicin In 14 Patients With Advanced Solid Tumors*," Cancer Res., 56:4686-4693; Lemke, M. I. et al., (2004) "*MRI After Magnetic Drug Targeting In Patients With Advanced Solid Malignant Tumors*," Eur. Radiology, 14:1949-1955) in Germany, the location of advanced and unsuccessfully pretreated cancers or sarcomas is known, a ferrofluid consisting of nanoparticles coated with a chemotherapy drug (e.g. mitoxantrone or epirubicin) is injected into a vein, is circulated by the blood flow, and external magnets must then focus it to tumor locations. Thus it is necessary to concentrate a distributed ferrofluid to targets. This is more difficult than magnetically manipulating the location of a single object (as is done in all 3 examples above). Below data is presented demonstrating that dynamic magnetic actuation can still bypass Earnshaw's theorem for a distributed ferrofluid and enable its focusing to deep targets. Initial control results are presented along with a discussion of real-time ferrofluid sensing and feedback control.

Modeling

To rationally design dynamic actuation to focus a ferrofluid to deep targets, a mathematical model of how time-varying actuation will transport the fluid is employed. The model developed and implemented herein is the simplest one that contains the essential features: dynamic magnetic actuation and the resulting ferrofluid transport.

This model is similar to the one in Grief (Grief, A. D. et al. (2005) "*Mathematical Modelling Of Magnetically Targeted Drug Delivery*," J. of Magnetism and Magnetic Materials, 293:455-463) with the difference that we have gone beyond analytical solutions for simple cases and implemented ours numerically (in COMSOL):

$$\nabla \cdot \vec{B} = 0 \text{ and } \nabla \times \vec{H} = \vec{j} \tag{3}$$

$$\frac{\partial}{\partial t} \underbrace{C(\vec{r}, t)}_{\text{Ferrofluid Concentration}} = -\nabla \cdot \left[ C(\vec{r}, t) \underbrace{\vec{V}_{blood}(\vec{r}, t)}_{\text{Blood Convection}} - \underbrace{D(\vec{r})}_{\text{Diffusion}} \nabla C(\vec{r}, t) + \underbrace{k(\vec{r})}_{\substack{\text{Magnetic}\\\text{Drift}\\\text{Coefficient}}} C(\vec{r}, t) \underbrace{\nabla (|\vec{H}(\vec{r}, t)|^2)}_{\text{Control}} \right] \tag{8}$$

Equation (3), the magneto-static version of Maxwell's equations is appropriate: the employed actuation will be quasi-steady compared to radio frequencies. Here B is the magnetic field [in Tesla] with $B=\mu_0(H+M)=\mu_0(H+\chi H)$ where M is the material magnetization, H is the magnetic intensity [Amperes/meter], $\chi$ is the magnetic susceptibility of the particles (non-dimensional), and j is the current density [A/m$^2$] within the electromagnets.

In Equation (8), C is the concentration of ferrofluid in the body as a function of time t and space $\vec{r}=(x, y, z)$. The rate of change of this concentration is given by the gradient $\nabla$ of the flux which has three terms. 1) Convection of particles by the blood flow velocity $V_{blood}$; 2) Diffusion of the particles within the blood stream. For spherical nanoparticles in blood at body temperature, Brownian diffusion can be calculated by Einstein's law, but, as noted by Grief (Grief, A. D. et al. (2005) "*Mathematical Modelling Of Magnetically Targeted Drug Delivery*," J. of Magnetism and Magnetic Materials, 293:455-463), red blood cell collisions serve to further scatter the particles, and this scattering can be modeled as additional diffusion. 3) Magnetic drift. The applied magnetic field H($\vec{r}$,t) creates an additional velocity of the nanoparticles relative to the blood flow. Its size is determined by the balance between the applied magnetic force and the opposing viscous forces: the coefficient is: $k=(a^2/9\eta) \mu_0\chi/(1+\chi/3)$ where a is radius of the particles, $\eta$ is the viscosity of blood, $\mu_0=4\pi\times10^{-7}$ V s/A m is the permittivity of vacuum, and H is the externally applied magnetic field intensity. The k coefficient is treated as a constant here even though it can vary due to Stokes drag wall effects (slightly higher drag near blood vessel walls) and potentially due to some amount of particle chaining or aggregation (typically not seen to be significant in Luebbe's animal and human trials, thus Equation (8) does not yet include microscopic agglomeration forces).

As written, the model of Equation (8) is for transport within the vasculature. In surrounding tissue there would be an equivalent partial differential equation but with no blood convection terms and with different (lower) effective diffusion coefficients (Saltzman, W. M. (2001) DRUG DELIVERY: ENGINEERING PRINCIPLES FOR DRUG THERAPY, Oxford University Press, USA). Then there would have to be an extravasation term that described ferrofluid transport from blood to surrounding tissue. This level of detail also has not yet been included in the modeling.

This model is currently implemented in 2 spatial dimensions in COMSOL via a Matlab script that allows inclusion of feedback control—it allows magnetic actuation to be set by control algorithms that have access to the ferrofluid distribution at each time. The magneto-static equations are written in vector potential form and the convection-diffusion equation is in conservative weak form and contains a small amount of Petrov-Gallerkin streamline diffusion to prevent numerical instabilities. Both are solved simultaneously using $6^{th}$ order Lagrange-cubic finite elements. The model can handle any time-varying control inputs, pre-planned or due to closed-loop feedback control, but it smoothes out sharp jumps in time, such as suddenly turning on a magnet, over a small interval. Typically, the model has ~3,000 mesh points and runs in minutes to a few hours on a personal computer (depending on the complexity of the control algorithm). For the control case below the model is solved in non-dimensional parameters and there is no blood flow velocity yet ($V_{blood}=0$) since the goal is to demonstrate the ability to focus a distributed ferrofluid without any disturbances due to convection.

Figure 5:
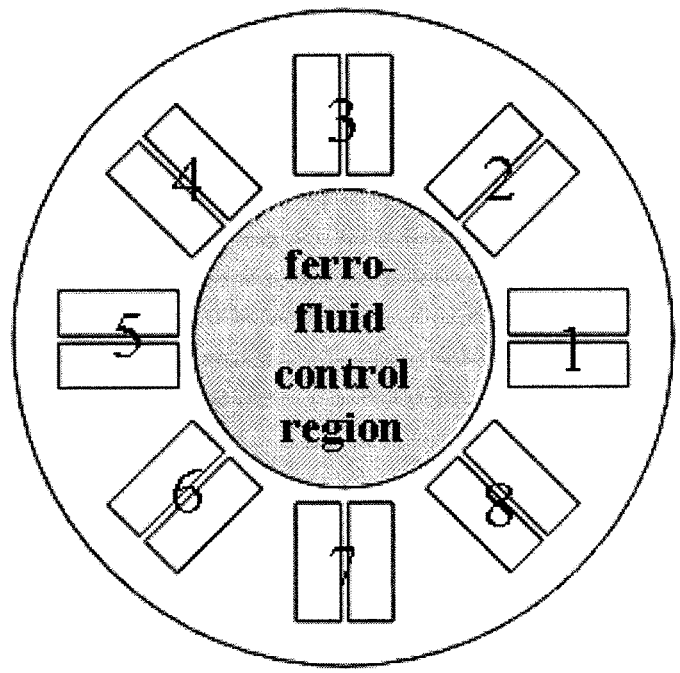
FIG. 5 shows a preferred model setup. Equation (3) is solved everywhere in the simulation domain which includes the 8 controlled magnets and an inner domain where ferrofluid transport takes place (Equation (3) and (8)).

Non-dimensional parameters for the simulation were set at diffusion D=1 and magnetic drift coefficient k=1000 with initial conditions C(x,y,0)=1. The eight magnets (FIG. 5) were spaced out equally at a radius of 1.5 (origin to center of each magnet) had a length of 0.8 and a width of 0.35 (0.15 for each half of the coil with a 0.05 gap). The electromagnets were actuated by imposing opposing vertical currents through the two coil halves: in FIG. 6 an inward arrow −1 actuation means that the half-coil in the clockwise direction had a −1 (down) current and the other coil had a +1 (up) current; vice versa for a reversed polarity (outward +1) actuation. For numerical stability, the compensated Petrov-Galerkin streamline diffusion parameter was $\delta_{SD}=0.5$.

Magnetic Control

Figure 6:
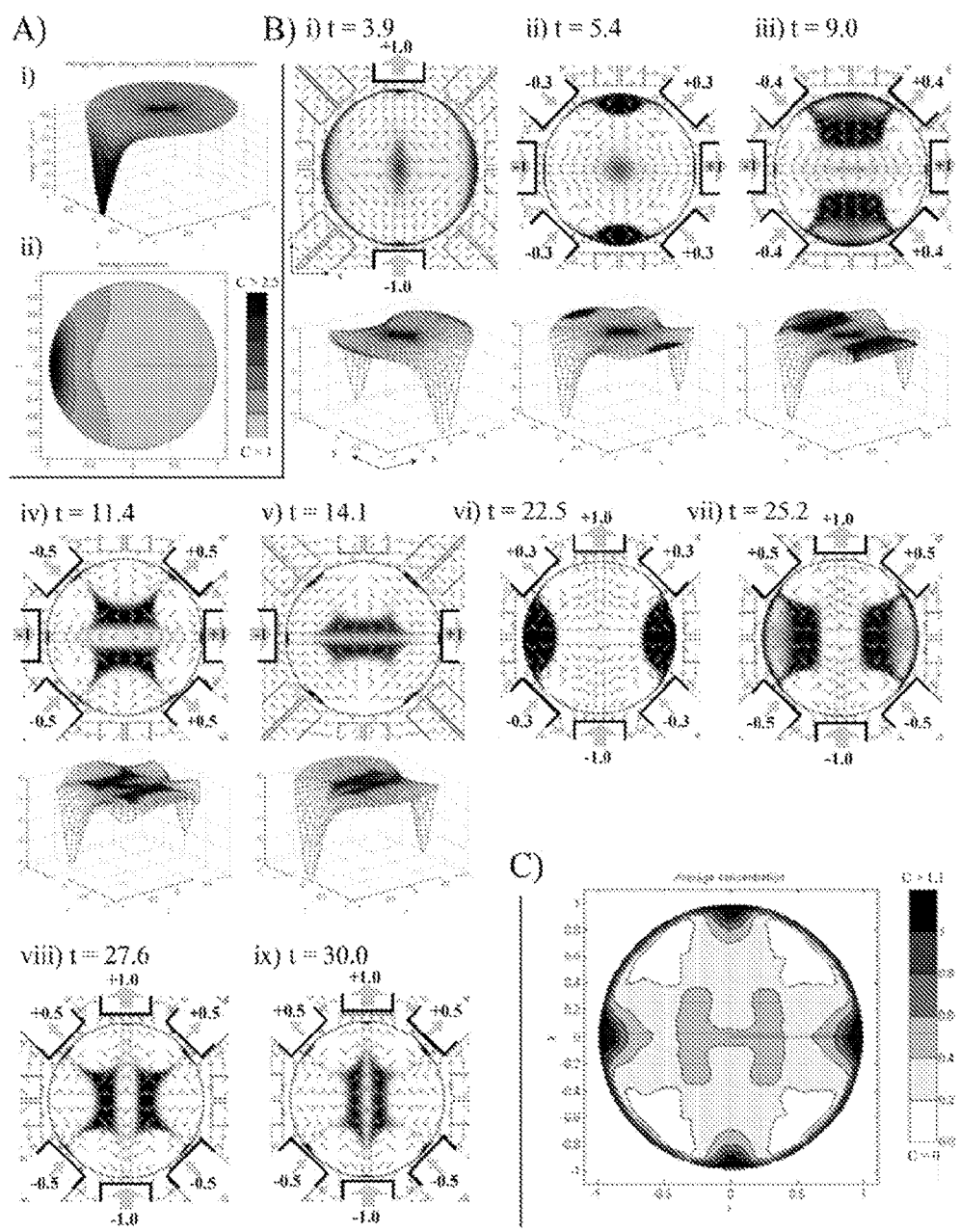
FIG. 6 (Panels A-C): Panel A shows constant actuation: ferrofluid transport due to turning on the 5th (far left) magnet. Sub-Panel i) The magnetic energy surface $U=-kH^2$ is plotted along the z axis to show ferrofluid flowing downhill along the force directions $F=-\nabla U$ with the resulting averaged concentration shown by the grayscale coloring here and in Sub-Panel ii). Panel B shows dynamic control: magnets are now turned on and off to transport ferrofluid to the center. The first 5 Sub-Panels (i-v) show ferrofluid concentration and magnetic actuation with the corresponding magnetic energy surfaces. Energy surfaces for the last 4 panels are 90 degree flips of the ones shown. Grayscale coloring denotes concentration (scale bar same as in Panel C). On magnets are illustrated by heavy black lines with weighted thick gray arrows and numbering showing magnet strength and orientation (South to North outwards is a positive polarity). Thin gray arrows (normalized to unit length) show magnetic force directions which match the gradients of the magnetic energy surfaces (forces point down the surfaces). Panel C shows the resulting time-averaged ferrofluid concentration. Note the on-average hot spot at the center target.

FIG. 6, Panel A shows the response of the ferrofluid to a single magnet that is turned on and left on. This simulation begins with a uniform ferrofluid concentration at time zero: $C(x,y,0)=1$. Fluid moves towards the highest magnetic field amplitude squared (to the maximum of $H^2$) and collects as close to this maximum as possible. If all 8 magnets were turned on and left on, the ferrofluid would collect at 8 spots nearest to the 8 magnets. This would also create a transient hot spot at the center since fluid there would be removed last. Creating such a "focus" by depleting ferrofluid everywhere else is not a viable in-vivo targeting approach since blood flow would quickly wash away this remaining region of the ferrofluid. Instead, our goal is to actively move ferrofluid to the deep target.

Application of the first dynamic control algorithm of the present invention is shown in FIG. 6, Panel B. At time t=0, the y-axis magnets (3rd and 7th) are turned on along the same direction (i.e. opposite polarity in the convention of FIG. 6) with unit strength. This creates the highest magnetic field along the y axis, and along this axis, the field is highest nearest the two on magnets. The resulting magnetic energy surface is a saddle, as shown in FIG. 6, Panel B, Subpanel i (bottom). Fluid flows down this saddle: it forms a transient hot-spot at the center (where depletion is slowest) and collects near the two on magnets.

The key challenge now is to get the ferrofluid out from near the two y-axis magnets and moving towards the center. To do so, at time t=4, the 8 magnets are switched to values u=[+1,+0.3,0,−0.3,−1,−0.3,0,+0.3] as shown in FIG. 6, Panel B, Subpanel ii. The extra |0.3| values of magnets 2, 4, 6, and 8 create two local unstable (energy maxima) along the y axis just outside the ferrofluid hot spots (see the force arrow sources in FIG. 6, Panel B, Subpanel ii adjacent to magnets 3 and 7) and they cause the ferrofluid to spill down the energy surface towards the center target.

Ferrofluid continues to move in along the y axis but by t=9 there is a significant amount of spreading out along the x direction, towards magnets 1 and 5 (looking at the energy surface in FIG. 6, Panel B, Subpanel iii, it is visible how the ferrofluid hot spot is on a surface that is curved along the x direction). To combat this, magnets 2, 4, 6 and 8 are turned on to higher values (this switch from |0.3| to |0.5| happens smoothly from t=8.9 until t=9.1) which flattens out the energy surface in x somewhat (FIG. 6, Panel B, Subpanel iv) limiting further spread in x but continuing to drive the fluid in along y.

By t=14.1, the ferrofluid hot spot has reached the center target but has nevertheless spread significantly in x. The x axis magnets 1 and 5 are now turned on, at t=14, to create foci near those magnets. The sequence then repeats in the x direction: place saddles outside the foci to drive them back in (t=20) and flatten the energy surface in the y direction at t=25 to limit spreading in the y direction. The results, both in terms of ferrofluid concentration and the energy surface are 90 degree flips of those already shown in the y direction. As this sequence repeats the control scheme continually drives ferrofluid through the center thus creating a hot spot on average at the central target (as shown in FIG. 6, Panel C).

This control algorithm was chosen by hand and may be further optimized. For example, optimization problems may be phrased to optimize each step (shape foci at edges, move to center, prevent spread in other directions, repeat). For example, maximizing fluid transport from a current hot spot to a neighboring target region or way point, the move problem, can be cast as a quadratic optimization program. Instead of choosing values for the side-magnets (2, 4, 6, and 8 above) by hand to flatten out a region, the magnet values may be optimally chosen. It is also clear how the control schemes can be extended to deal with a disturbing convective flow. Energy surfaces can be shaped and re-oriented to bring the fluid back as it is disturbed. More sophisticated control schemes will correct the location of hot spots and also refocus them. For example, initial optimization results show that it is possible to move and shorten hot spots along their longest axes—by placing energy maxima or saddles behind them to cause the tail end to catch up with the front end.

The In Vivo Problem

The in-vivo deep-target control problem has many more factors than those addressed in the starting simulations and initial control scheme above. Although the mathematics of the control problem (focusing a distributed fluid to an internal target) is non-standard and difficult and there are no existing control methodologies to do this, the focusing of magnetic chemotherapy in humans has been achieved for shallow targets (Lubbe, A. S. et al. (1996) "*Preclinical Experiences With Magnetic Drug Targeting: Tolerance And Efficacy*," Cancer Res., 56:4694-4701; Lubbe, A. S. et al. (1996) "Clinical Experiences With Magnetic Drag Targeting: A Phase I Study With 4'-*Epidoxorubicin In* 14 *Patients With Advanced Solid Tumors*," Cancer Res., 56:4686-4693; Lemke, M. I. et al., (2004) "*MRI After Magnetic Drug Targeting In Patients With Advanced Solid Malignant Tumors*," Eur. Radiology, 14:1949-1955), and the principles of the present invention enable such application to deep targets.

Vasculature geometry and blood flow will vary from patient to patient and, with the possible exception of major vessels visualized by MRI, will not be known in a clinical setting. The goal is therefore to use applied (thus known) magnetic fields to manipulate the ferrofluid and, as unknown blood forces disturb it, to continuously put it back to the deep tumor (feedback control). Patient-to-patient vascular geometry variation will not prevent this task in the following sense. Metabolically active cells are within <100 μm of blood vessels (Saltzman, W. M. (2001) Drug Delivery: Engineering Principles for Drug Therapy, Oxford University Press, USA), so the length scale of vasculature connectivity is generally very small compared to the desired focusing length scale (focusing to a deep target centimeters across would be a dramatic achievement). If there is a concentration of ferrofluid to the right of the target, and a magnetic force is applied to move it left, there should be enough vasculature connectivity to allow the ferrofluid to find a path from right to left. When there is insufficient vasculature connectivity, the control algorithm will see that the fluid is not moving back to its target, and will take corrective actions to circumvent obstructions.

Figure 7:
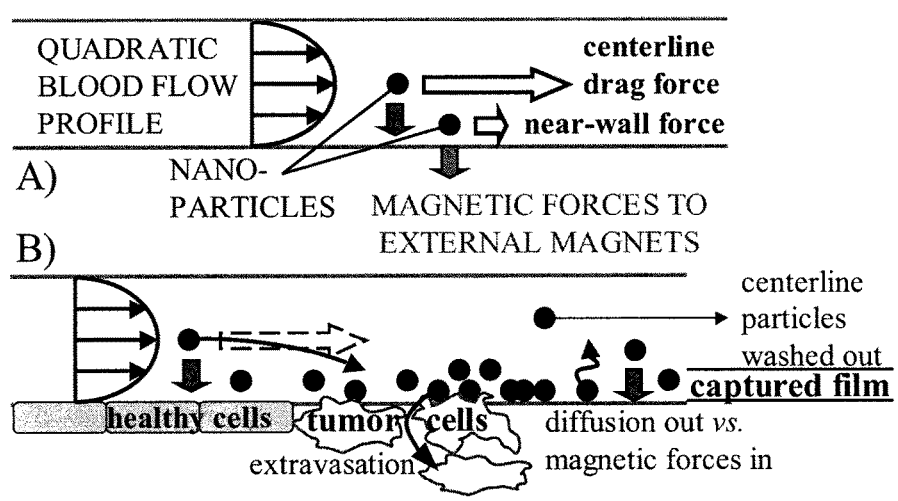
FIG. 7, Panels A-B show the magnetic and blood drag forces on nano-particles. Panel A shows the quadratic flow profile in a blood vessel creates large drag forces on particles at the centerline but only small forces on particles near the vessel wall. Panel B shows that nano-particle capture will occur in a thin film at vessel walls but the thickness of the film will depend on the blood flow velocity and the strength of the magnetic field gradient (in small capillaries the blood flow profile shape is more blunted). In blood-cell diameter micro-capillaries where red blood cells pass through in single file, a blood flow "velocity profile" is not defined.

The issue of sufficient magnetic forces versus blood convection forces is subtle. Blood drag flow forces vary with particle position in the blood vessel: a particle at the vessel center-line will see a high velocity and hence high drag force, but a particle near the blood vessel wall will see a near zero velocity (due to the no-slip boundary condition at the wall) and can be held by a small magnetic force (FIG. 7). Trapping of a particle in a blood vessel occurs if the magnetic field pulls the particle out of the strong center-line flow before it leaves the vessel (Voltairas, P. A. et al. (2002) "*Hydrodynamics Of Magnetic Drug Targeting*," Journal of Biomechanics, 35:

813-821; Mikkelsen, C. I. (2005) *"Magnetic Separation And Hydrodynamic Interactions In Microfluidic Systems,"* Ph.D. Thesis, Department of Micro and Nanotechnology; Lyngby, Denmark: Technical University of Denmark). Thus, when nano-particles are trapped, they are confined in thin films at the inside boundaries of blood vessels, which is exactly where they must be to subsequently be taken up by surrounding tissue. It is these thin films of nano particles that we must continuously put back to deep tumor locations by dynamic control.

Initial calculations show that, using MRI-strength magnets, there should be sufficient force to actuate nano-particles, even at 20-30 cm depths. In humans, blood flow velocities range from >I m/s highest peak velocity in the ascending aorta to ~30 cm/s in main blood return arteries to <5 mm/s in arterioles and venules (Voltairas, P. A. et al. (2002) *"Hydrodynamics Of Magnetic Drug Targeting,"* Journal of Biomechanics, 35: 813-821; Grief, A. D. et al. (2005) *"Mathematical Modelling Of Magnetically Targeted Drug Delivery,"* J. of Magnetism and Magnetic Materials, 293:455-463; Saltzman, W. M. (2001) DRUG DELIVERY: ENGINEERING PRINCIPLES FOR DRUG THERAPY, Oxford University Press, USA; Ganguly, R. et al. (2005) *"Analyzing Ferrofluid Transport For Magnetic Drug Targeting,"* J. of Magnetism and Magnetic Materials, 289: 331-334). Magnetic forces will not capture particles against the high flow rates in major arteries, instead, focusing will have to be carried out by thin films moving along secondary blood vessels (as does happen in animals and humans for successful focusing to shallow targets). Computing the distance from the vessel wall in a quadratic flow profile where blood drag-flow forces can first overcome the applied magnetic force and wash away the particles, for a 4 Tesla magnet and accounting for particle magnetic saturation, a ferrofluid film of a micrometer to a few hundred nanometer thickness should form in capillaries 20 cm to 30 cm deep. Particle chaining and agglomeration, to the degree that they may occur in-vivo, may also increase forces by allowing magnetic forces to act on particles in small groups.

Deep in-vivo real-time ferrofluid sensing for feedback control can be achieved by making the particles slightly radioactive (see, Kim C.-O. et al. (United States Patent Publication No. 2005/0019257), so that their position can be detected by next-generation gamma cameras. The radiation dose absorbed by the body during such nuclear imaging is small, far less than an x-ray. CMOS gamma cameras for high-speed imaging are being developed by Westbrook (Parker, S. I. et al. (2006) *"3DX: An X-Ray Pixel Array Detector With Active Edges,"* IEEE Transactions on Nuclear Science, 53:1676-1688; Kenney, C. J. et al. (2006) *"Active-Edge Planar Radiation Sensors,"* Nuclear Instruments and Methods in Physics Research A, 565:272-277). These cameras function at >10 kHz (far in excess of the speeds we need to combat the ~1 Hz heart-rate blood-flow disturbances in humans), their pixels can be tilted and tiled without gaps, and can be batch fabricated at reasonable cost. It is possible to coat the inside of a sphere or tube with these pixels to form a gamma "camera" that would have near complete solid angle viewing (except for obstructions). Initial calculation show that such cameras are able to detect magnetic nano-particles at concentrations that have been used in human trials (Lubbe, A. S. et al. (1996) *"Preclinical Experiences With Magnetic Drug Targeting: Tolerance And Efficacy,"* Cancer Res., 56:4694-4701; Lubbe, A. S. et al. (1996) *"Clinical Experiences With Magnetic Drug Targeting: A Phase I Study With 4'-Epidoxorubicin In 14 Patients With Advanced Solid Tumors,"* Cancer Res., 56:4686-4693; Lemke, M. I. et al., (2004) *"MRI After Magnetic Drug Targeting In Patients With Advanced Solid Malignant Tumors,"* Eur. Radiology, 14:1949-1955). Or, as pointed out by Martel (Martel, S. et al. (2007) *"Automatic Navigation Of An Untethered Device In The Artery Of A Living Animal Using A Conventional Clinical Magnetic Resonance Imaging System,"* Applied Physics Letters 90:114105; Mathieu, J. B. et al. (2007) *"Magnetic Microparticle Steering Within the Constraints of an MRI System: Proof of Concept of a Novel Targeting Approach,"* Biomedical Microdevices, 9:801-808), magnetic fields can be duty cycled to both actuate (control mode) and sense (MRI mode) but this leads to a loss in control effectiveness since part of each cycle is devoted to sensing.

Unless magnets or magnetic materials are surgically implanted in patients, which is undesirable and often not clinically feasible, magnetic drug delivery is presently limited to shallow targets (typically <5 cm depth with the strongest possible, still safe, magnetic fields). The dynamic control of magnets that is provided by the present invention permits one to focus magnetic carriers to deep tissue targets. Based on the above-described first-principles magneto-statics and ferrofluid transport model, the invention has demonstrated that a sequence of actuations can drive ferrofluid always through a center region thus creating a focus at this deep target on average.

In sum, the present invention demonstrates that magnetic drug delivery is able to target therapy to specific regions in the body, improving efficacy and reducing side effects for treatment of cancer, stroke, infection, and other diseases. Using stationary external magnets, which attract the magnetic drug carriers, this treatment has been limited to shallow targets (<5 cm below skin depth using the strongest possible, still safe, practical magnetic fields). The results presented for the dynamic magnetic actuation of the present invention indicates that it is possible to vary magnets one against the other to focus carriers between them on average.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for treating a patient comprising the steps of:
   (A) administering a ferrofluid comprising a plurality of magnetizable objects to a patient;
   (B) applying a dynamic magnetic field to the patient using external magnets;
   (C) sensing and monitoring over time locations of the plurality of magnetizable objects within the patient;
   (D) shaping the applied dynamic magnetic field in three spatial dimensions over a period of time space and time using a feedback control algorithm that dictates actuation and strength of the external magnets in response to said sensing and monitoring; and
   (E) directing and focusing a selected concentration of the plurality of magnetizable objects within the ferrofluid to a deep target area within the patient in response to said shaping the applied dynamic magnetic field.

2. The method of claim 1, wherein said ferrofluid comprises a therapeutic, diagnostic, visualization or prophylactic agent.

3. The method of claim 1, wherein said plurality of magnetizable objects are coupled to a therapeutic, diagnostic, visualization or prophylactic agent.

4. The method of claim 1, wherein said deep target area is at least 5 centimeters inside the patient.

5. The method of claim 1, wherein said magnetizable objects are between about 1 nm and 1 mm in diameter.

6. The method of claim 5, wherein said magnetizable objects are between about 1 μm and 1 nm in diameter.

7. The method of claim 1, wherein said administering step comprises injecting said plurality of magnetizable objects into the patient.

8. The method of claim 1, wherein said magnetizable objects comprise a therapeutic, diagnostic, visualization or prophylactic agent.

9. The method of claim 1, wherein said magnetizable objects comprise a detectable label.

10. The method of claim 9, wherein said detectable label is a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label.

11. The method of claim 1, wherein said dynamic magnetic field has a rate of change of up to about 20 Tesla/second.

12. The method of claim 1, wherein said deep target area is associated with a cancer, a disease of the vascular system, an infection, or non-cancerous disease material.

13. The method of claim 12, wherein said deep target area is located at least 5 centimeters inside the patient.

14. The method of claim 1, wherein said sensing and monitoring step comprises using magnetic resonance imaging.

15. The method of claim 1, further comprising a feedback controller to control the dynamic magnetic field in response to said sensing and monitoring.

16. The method of claim 1, wherein an effectiveness of said selected concentration of the plurality of magnetizable objects for treating the patient is measured over a period of time.

17. The method of claim 1, wherein said shaping step comprises controlling the external magnets in time.

18. A method for treating a patient consisting essentially of the steps of:
(A) administering a ferrofluid comprising a plurality of magnetizable objects to a patient;
(B) applying a dynamic magnetic field to the patient using external magnets;
(C) sensing and monitoring over time locations of the plurality of magnetizable objects within the patient;
(D) shaping the applied dynamic magnetic field in three spatial dimensions over a period of time using a feedback control algorithm that dictates actuation and strength of the external magnets in response to said sensing and monitoring; and
(E) directing and focusing a selected concentration of the plurality of magnetizable objects within the ferrofluid to a deep target area within the patient in response to said shaping the applied dynamic magnetic field.

19. The method of claim 18, wherein said ferrofluid comprises a therapeutic, diagnostic, visualization or prophylactic agent.

20. The method of claim 18, wherein said plurality of magnetizable objects are coupled to a therapeutic, diagnostic, visualization or prophylactic agent.

21. The method of claim 18, wherein said magnetizable objects comprise a therapeutic, diagnostic, visualization or prophylactic agent.

22. The method of claim 18, wherein the deep target area is at least 5 centimeters inside the patient.

23. The method of claim 18, wherein said magnetizable objects are between about 1 nm and 1 mm in diameter.

24. The method of claim 23, wherein said magnetizable objects are between about 1 μm and 1 nm in diameter.

25. The method of claim 18, wherein said magnetizable objects comprise a detectable label.

26. The method of claim 25, wherein said detectable label is a radioisotopic label, a paramagnetic label, a CARS (coherent anti-Stokes Raman Spectroscopy)-detectable label, a multiphoton fluorescence microscopy-detectable label, a harmonic microscopy-detectable label, an acoustic imaging-detectable label, an impedance spectroscopy-detectable label or a reflectance spectroscopy-detectable label.

27. The method of claim 18, wherein said dynamic magnetic field has a rate of change of up to about 20 Tesla/second.

28. The method of claim 18, wherein said deep target area is associated with a cancer, a disease of the vascular system, an infection, or non-cancerous disease material.

\* \* \* \* \*